(12) United States Patent
Ragaglia et al.

(10) Patent No.: US 9,051,592 B2
(45) Date of Patent: Jun. 9, 2015

(54) METHODS OF GANGLIOSIDE PRODUCTION

(71) Applicant: Garnet BioTherapeutics, Inc., Malvern, PA (US)

(72) Inventors: Vanessa Ragaglia, Newtown Square, PA (US); Vandana Madanlal Sharma, Lafayette Hill, PA (US)

(73) Assignee: Garnet Biotherapeutics, Inc., Malvern, PA (US)

( * ) Notice: Subject to any disclaimer, the term of this patent is extended or adjusted under 35 U.S.C. 154(b) by 0 days.

(21) Appl. No.: 13/796,213

(22) Filed: Mar. 12, 2013

(65) Prior Publication Data

US 2013/0261067 A1 Oct. 3, 2013

Related U.S. Application Data

(63) Continuation of application No. 13/745,313, filed on Jan. 18, 2013.

(60) Provisional application No. 61/588,882, filed on Jan. 20, 2012.

(51) Int. Cl.
| | |
|---|---|
| C12P 1/00 | (2006.01) |
| C12N 5/00 | (2006.01) |
| C12P 19/44 | (2006.01) |
| A61K 31/7032 | (2006.01) |
| G01N 33/92 | (2006.01) |
| A61K 31/4706 | (2006.01) |

(52) U.S. Cl.
CPC ............. *C12P 19/44* (2013.01); *A61K 31/7032* (2013.01); *G01N 33/92* (2013.01); *A61K 31/4706* (2013.01)

(58) Field of Classification Search
CPC ................................. C12P 1/00; C12N 5/00
USPC .................................................. 435/41, 325
See application file for complete search history.

(56) References Cited

U.S. PATENT DOCUMENTS

| | | |
|---|---|---|
| 5,532,141 A | 7/1996 | Holler |
| 5,635,504 A | 6/1997 | Ryono et al. |
| 5,788,985 A | 8/1998 | Rodriguez et al. |
| 5,922,773 A | 7/1999 | Lipton et al. |
| 6,440,703 B1 | 8/2002 | DeFrees |
| 2002/0068080 A1 | 6/2002 | Lerner |
| 2003/0087396 A1 | 5/2003 | Saito |
| 2004/0157926 A1 | 8/2004 | Heresco-Levy et al. |
| 2005/0221380 A1 | 10/2005 | Muthing et al. |
| 2006/0142241 A1 | 6/2006 | Yoo |
| 2007/0117778 A1 | 5/2007 | Ilan |
| 2007/0224200 A1 | 9/2007 | Elbawab et al. |
| 2008/0064709 A1 | 3/2008 | Krishnan |
| 2012/0220543 A1 | 8/2012 | Schneider et al. |
| 2012/0220544 A1 | 8/2012 | Schneider et al. |
| 2012/0220763 A1* | 8/2012 | Schneider et al. .............. 536/53 |

FOREIGN PATENT DOCUMENTS

| | | |
|---|---|---|
| EP | 0661061 A3 | 12/1996 |
| EP | 2011799 A1 | 1/2009 |
| WO | WO 9803529 A1 | 1/1998 |
| WO | WO 2004/083387 A2 | 9/2004 |
| WO | WO 2007/006157 A1 | 1/2007 |
| WO | WO 2008/034815 A1 | 3/2008 |
| WO | WO 2011/028795 A2 | 3/2011 |

OTHER PUBLICATIONS

Yuyama et al. (Chloroquine-induced endocytic pathway abnormalities: Cellular model of GM1 ganglioside-induced Aβ fibrillogneesis in Alzheimer's disease. FEBS Letters 580 (2006) 6972-6976.*
Ackerman et al., "Differential expression of surface monosialoganglioside GM1 in various hemic cell lines of normal human bone marrow. A quantitative immunocytochemical study using the cholera toxin-gold-labeled anti-cholera toxin procedure," J. Histochem. Cytochem. 28:1334-1342 (1980).
Christie, "Ganglioside," The AOCS Lipid Library, last updated Jul. 23, 2012.
Dijkhuis et al., "Gangliosides do not affect ABC transporter function in hum,an neuroblastoma cells," J. Lipid Res. 47:1187-1195 (2006).
Freund et al., "Differential expression of biofunctional GM1 and GM3 gangliosides within the plastic-adherent multipotent mesenchymal stromal cell population," Cytotherapy 12:131-142 (2010).
Hirata et al., "Chloroquine inhibits glutamate-induced death of a neuronal cell line by reducing reactive oxygen species through sigma-1 receptor," J. Neurochem. 119:839-847 (2011).
Ikeda et al., "Targeted analysis of ganglioside and sulfatide molecular species by LC/ESI-MS/MS with theoretically expanded multiple reaction monitoring," J. Lipid Res. 49:2678-2689 (2008).
Kolter et al., "Combinatorial Ganglioside Biosynthesis," Journal of Biological Chemistry 277(29):25859-25862 (2002).
Kwak, et al., "Dynamic changes of gangliosides expression during the differentiation of embryonic and mesenchymal stem cells into neural cells," Exp. Mol. Med. 38(6):668-676 (2006).
Lauer et al., "Analysis of cholera toxin-ganglioside interactions by flow cytometry," Biochemistry 41:1742-1751 (2002).
Maccioni et al., "The biosynthesis of gangliosides. Labeling of rat brain gangliosides in vivo," Biochem J. 125:1131-1137 (1971).
Masserini and Freire, "Thermotropic Characterization of Phosphatidylcholine Vesicles Containing Ganglioside GM1 with Homogeneous Ceramide Chain Length," Biochem. 25:1043-1049 (1986).
Masson et al., "Glucosamine induces cell-cycle arrest and hypertrophy of messangial cells: implication of gangliosides," Biochem. J. 388:537-544 (2005).

(Continued)

*Primary Examiner* — Karen Cochrane Carlson
*Assistant Examiner* — Natalie Moss
(74) *Attorney, Agent, or Firm* — Fanelli Haag PLLC

(57) ABSTRACT

The invention provides methods for production of gangliosides, e.g., GM1, from cells in culture using, for example, bone marrow cells and neuroblastoma cells. Methods include the treatment of cells with neural induction media and chloroquine, or chloroquine alone in the case of, e.g., human bone marrow cells, neuraminidase or glucosamine, to induce the production of gangliosides, e.g., GM1, in the cells. Also provided are methods of long-term, high density culturing of cells without passaging to produce gangliosides, e.g., GM1. Methods of quantifying gangliosides, e.g., GM1 in cell culture are also provided.

7 Claims, 11 Drawing Sheets

(56) References Cited

OTHER PUBLICATIONS

Figure 1:
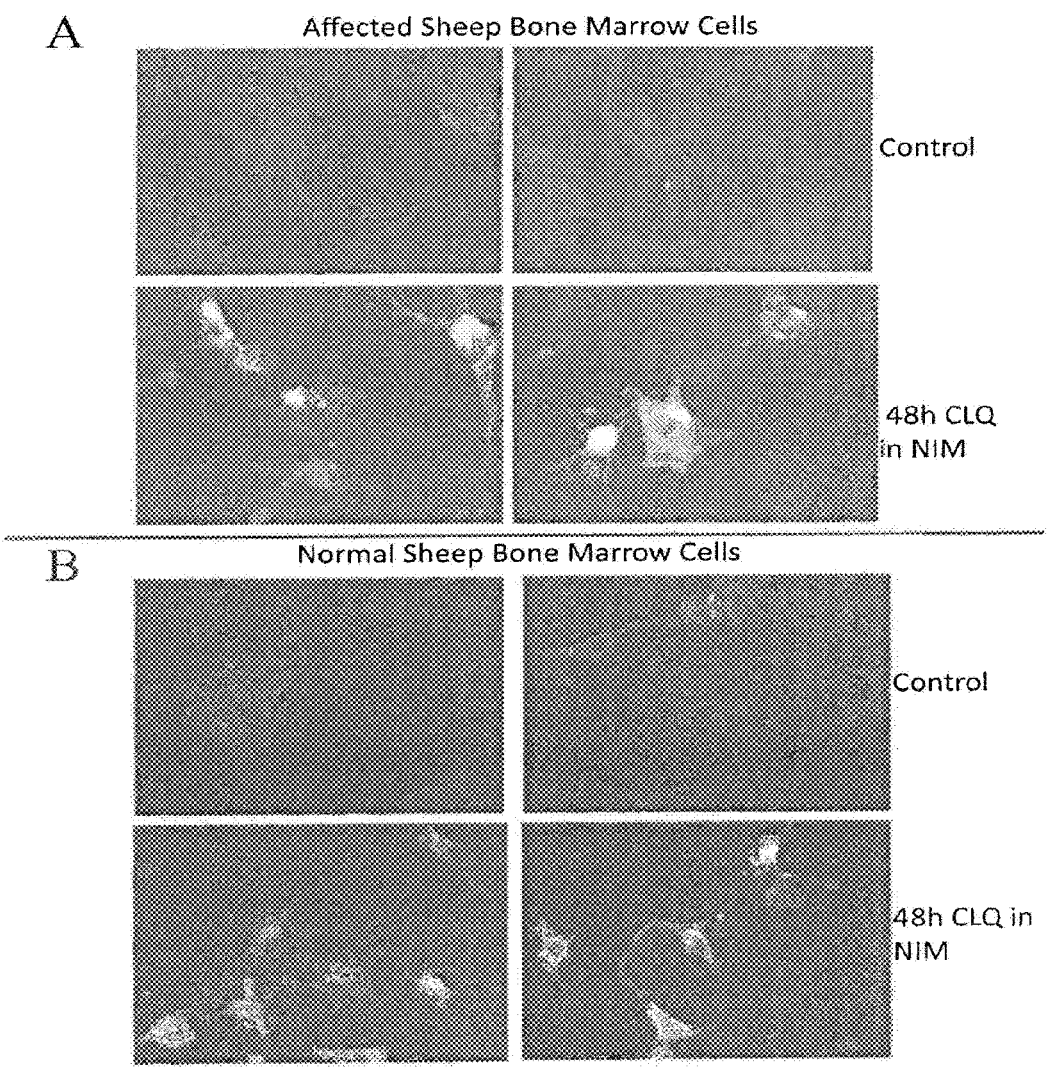

Miller-Podraza et al., "Biosynthesis and localization of gangliosides in cultured cells," Biochem. 21:3260-3265 (1982).
Nishio et al., "Overexpressed GM1 Suppresses Nerve Growth Factor (NGF) Signals by Modulating the Intracellular Localization and NGF Receptors and Membrane Fluidity in PC12 Cells," J. Biol. Chem. 279:33368-33378 (2004).
Parton, R.G., "Ultrastructural Localization of Gangliosides; GM1 Is Concentrated in Caveolae," J. Histochem. Cytochem. 42(2):155-166 (1994).
Ragaglia et al., U.S. Appl. No. 13/745,313, Jan. 18, 2013.
Ragaglia et al., U.S. Appl. No. 14/214,333, Mar. 14, 2014.
Schneider et al., "Parkinson's disease improved function with GM1 ganglioside treatment in a randomized placebo-controlled study," Neurology 50(6):1630-1636 (1998).
Schneider et al., "GM1 ganglioside in Parkinson's disease: results of a five year open study," J. Neurol. Sci. 292:45-51 (2010).
Sonnino and Chigorno, "Ganglioside molecular species containing C18- and C20-sphingosine in mammalian nervous tissues and neuronal cell cultures," Biochem. Biophys. Acta. 1469:63-77 (2000).
Taketomi et al., "Matrix-assisted laser desorption ionization time-of-flight mass spectrometric analysis of glycosphingolipids including gangliosides," Acta Biochem. Pol. 45 (4):987-999 (1998).
Tio et al., "Roles of db-cAMP, IBMX and RA in Aspects of Neural Differentiation of Cord Blood Derived Mesenchymal-Like Stem Cells," PLoS ONE 5(2):1-11 (2010).
Xu et al., "Multi-system disorders of glycosphingolipid and ganglioside metabolism," J. Lipid Res. 51:1643-1675 (2010).
Yuyama et al., "Accelerated release of exosome-associated GM1 ganglioside (GM1) by endocytic pathway abnormality: another putative pathway for GM1-induced amyloid fibril formation," Journal of Neurochemistry 105:217-224 (2008).
Yuyama et al., "Chloroquine-induced endocytic pathway abnormalities: Cellular model of GM1 ganglioside-induced fibrilogenesis in Alzheimer's disease," FEBS Lett. 580:6972-6976 (2006).
Svennerholm, J. Neurochem 10:613-623 (1963).
Ladisch, S., "Shedding and Immunoregulatory Activity of YAC-1 Lymphoma Cell Gangliosides," Cancer Research 43:3808-3813 (1983).
Kumbale et al., "GM1 Delivery to the CSF Via the Olfactory Pathway," Drug Delivery 6:23-30 (1999).
Peng et al., "Development of a Large Scale Process for the Conversion of Polysialogangliosides to Monosialotetrahexosylganglioside with a Novel *Brevibacterium casei* Producing Sialidase," Biotechnol Letters 29:885-889 (2007).
Osborne et al., "Neuroprotection in Relation to Retinal Ischemia and Relevance to Glaucoma," Survey of Opthamology 43(1):S102-S128 (1999).
Dreyfus et al., "Gangliosides and Neurotrophic Growth Factors in the Retina," Annals of the New York Academy of Sciences 845(1):240-252 (1998).
Norido et al., "Monosialoganglioside (GM1) Treatment of Ouabain-Induced Retinopathy in the Rabbit," Acta Neuropathological 62(1/2):46-50 (1983).
Schneider, JS, "GM1 Gangligoside in the Treatment of Parkinson's Disease," Annuals of New York Academy of Sciences, 845(1):363-373 (1998).
Ariga et al., "Role of Ganglioside Metabolism in the Pathogenesis of Alzheimer's Disease—A Review," Journal of Lipid Research 49(6):1157-1175 (2008).
Rothblat et al., "The Effects of L-Deprenyl Treatment, Alone and Combied with GM1 Ganglioside, on Striatal Dopamine Content and Substantia Nigra Pars Compacta Neurons," Brain Research 799(1/2):226-230 (1998).
New, P., "Radiation Injury to the Nervous System," Current Opinion in Neurology 14(6):725-734 (2001).
Ledeen et al., "Gangliosides as Neurotrophic Agents: Studies on the Mechanism of Action," Acta Neurobiol Exp. 50:439-449 (1990).
Di Gregorio et al., "Efficacy of Ganglioside Treatment in Reducing Functional Alterations Induced by Vincristine in Rabbit Peripheral Nerves," Cancer Chemother. Pharmacol. 26:31-36 (1990).
Pinsky et al., "GM1 Gangliosides in Skin Fibroblast Culture: Enzymatic Differences between Types 1 and 2 and Observations on a Third Variant," Am. J. Hum. Genet. 26:563-577 (1974).
Vanna Chigorno et al., "Formation of a Cytosolic Ganglioside-Protein Complex Following Administration of Photoreactive Ganglioside GM1 to Human Fibroblasts in Culture," FEBS 263(2):329-331 (1990).
Gu et al., "Silencing of GM3 Synthase Suppresses Lung Metastasis of Murine Breast Cancer Cells," online at http://breast-cancer-research.com/content/10/1/R1 at 1-12 (2008).
Parrinello et al, "Oxygen Sensitivity Severely Limits the Replicative Lifespan of Murine Fibroblasts," Nature Cell Biology 5(8):741-747 (2003).

* cited by examiner

METHODS OF GANGLIOSIDE PRODUCTION

BACKGROUND OF THE INVENTION

1. Field of the Invention

The present invention relates to methods of producing gangliosides, e.g., GM1, from cells grown in culture. In particular, cells are treated chemically and/or biochemically manipulated to induce the production of gangliosides, e.g., GM1, and/or cells are cultured long-term at high density, without passaging, to accumulate gangliosides, e.g., GM1.

2. Background Art

GM1 Ganglioside Structure and Function

GM1 is a monosialoganglioside having the following structure:

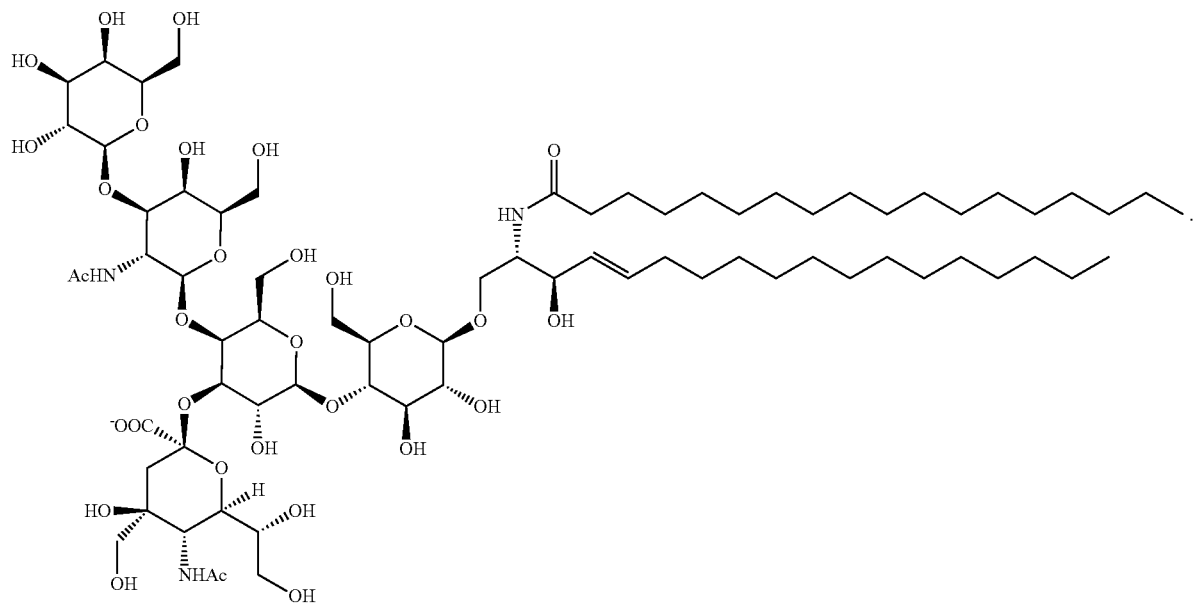

GM1 is a constituent of nerve cell membranes, is known to modulate a number of cell surface and receptor activities, and plays important roles in neuronal differentiation and development, protein phosphorylation and synaptic function. GM1 therefore impacts neuronal plasticity and repair mechanisms, and the release of neurotrophins in the brain. In addition to its role in the nervous system, GM1 is involved in internalization of pathogens, cell signaling, proliferation, survival and differentiation. It is a component of lipid rafts, a microdomain within the plasma membrane that is enriched in cholesterol and sphingolipids. Furthermore, GM1 is involved in activation of a sodium-calcium exchanger in the inner membrane of the nuclear envelope. Its interaction with the calcium exchanger modulates nuclear and cellular calcium. In addition to its function in cellular physiology, GM1 acts as the site of binding for cholera toxin.

GM1 has been shown to be effective in treating different types of central nervous system lesions in experimental animals, resulting in significant biochemical and behavioral recovery. Moreover, pretreatment with GM1 inhibits damage resulting from a variety of neurotoxin exposures.

GM1 has also been shown to be effective in the short-term treatment of Parkinson's disease subjects, resulting in significant symptom reduction. Schneider et al., *Neurology* 50:1630-1636 (1998). A more recent five-year study indicates that long-term GM1 use by Parkinson's disease subjects is safe and may provide some clinical benefit for these subjects. Schneider et al., *J. Neurol. Sci.* 292:45-51 (2010), incorporated herein by reference in its entirety. It is uncertain how GM1 exerts potential neuroprotective, neurorestorative or neurorescue effects on the dopamine system. Id. at 50. However, it is speculated that GM1 incorporated in neuronal plasma membranes may alter the stability of lipid rafts and therefore promote a variety of beneficial cellular processes. Id.

Gangliosides

Gangliosides are a major glycosphingolipid in mammals, containing sugar chains with different numbers of sialic acid residues. Many different subspecies of sugar exists in gangliosides. Gangliosides are implicated in a number of diseases and disorders, including Tay-Sachs disease, Parkinson's disease, Alzheimer's disease and cancer, among others.

The biosynthesis of gangliosides are closely interconnected through the use of common biosynthetic enzymes and substrates. For example, the production of GM1 relies on the enzyme galactosyltransferase II, commonly used to produce other gangliosides, e.g., GA1, GD1b and GT1c. Xu et al., *J. Lipid Res.* 51:1643-1675 (2010), incorporated herein by reference in its entirety. Because of their common structural features and components, new gangliosides are often synthesized from recycled components of degraded gangliosides, in particular ceramide and sphingosine. Id. For example, core molecules such as ceramide, galactose, GalNAc, sialic acid, are required for synthesis of gangliosides. Id. As a result, factors that influence the production or degradation of one member of the ganglioside family frequently alter the production and degradation of other gangliosides. For example, because GM1 is the precursor to GD1a, increases in GM1 will favor the production of GD1a for the cell to maintain a normal or balanced proportion of gangliosides. Mason et al., *Biochem. J.* 388:537-544 (2005); Miller-Podraza et al., *Biochem.*

21:3260-3265 (1982); Nishio et al., *J. Biol. Chem.* 279: 33368-33378 (2004), each of which is herein incorporated by reference in its entirety.

GM1 Production

GM1 derived from the bovine brain has been used clinically in the past. See, e.g., Schneider et. al., *J. Neurol. Sci.* 292:45-51, 46 (2010) ("Patients self-administered . . . bovine brain-derived [GM1] sodium salt . . . "), incorporated herein by reference in its entirety. However, the limited yield of GM1 per bovine brain and the cost of producing GM1 in this manner has restricted the amount of GM1 available for commercial clinical use. In addition, diseases such as bovine spongiform encephalopathy, i.e., mad cow disease, have raised concerns regarding the safety of this source of GM1. While extraction of GM1 from the brains of sheep afflicted with GM1 gangliosidosis has also been described (see, e.g., U.S. Pat. No. 5,532,141), incorporated herein by reference in its entirety, such a method raises similar concerns regarding yield, cost and safety.

A clear, unmet need therefore exists for a cost-effective, high-yield and safe alternative to making GM1 for commercial clinical use.

BRIEF SUMMARY OF THE INVENTION

The invention provides a method of producing a ganglioside in a cell, comprising treating said cell with chloroquine ("CLQ") to accumulate said ganglioside; isolating said ganglioside; quantifying said ganglioside, or both, from said CLQ-treated cell; wherein said cell is selected from the group consisting of an immortalized cell, a stromal cell, and a fibroblast; wherein said cell is not a PC12 cell, an HT22 cell, a brain cell from a sheep afflicted with gangliosidosis, and a fibroblast cell from sheep afflicted with gangliosidosis.

The invention further provides methods of producing GM1 ganglioside comprising isolating bone marrow cells from sheep; culturing the sheep bone marrow cells in neuronal-induction media ("NIM") to produce neuron-like sheep bone marrow cells; treating the neuron-like sheep bone marrow cells with CLQ to accumulate GM1; and quantifying GM1, isolating GM1, or both, from the CLQ-treated neuron-like sheep bone marrow cells.

The invention further provides a method of producing GM1 ganglioside comprising treating human bone marrow cells with CLQ to accumulate GM1; and isolating GM1, quantifying GM1, or both, from the CLQ-treated human bone marrow cells.

The invention further relates to treating cells, e.g., bone marrow cells, with neuraminidase to accumulate gangliosides, e.g., GM1, in the cells, and isolating gangliosides, quantifying gangliosides, or both, from the neuraminidase-treated cells.

The invention further relates to treating cells, e.g., bone marrow cells, with glucosamine to accumulate gangliosides, e.g., GM1, in the cells, and isolating gangliosides, quantifying gangliosides, or both, from the glucosamine-treated cells.

The invention further relates to biochemically manipulating cells, e.g. primary cells or cell lines, to accumulate gangliosides, e.g., GM1, in the cells, and isolating gangliosides, quantifying gangliosides, or both, from the biochemically modified cells.

Also provided by the invention are methods of producing gangliosides, e.g., GM1, by culturing cells without passaging and at high density to accumulate said ganglioside.

The invention also relates to methods of quantifying an amount of gangliosides, e.g., GM1, in a population of adherent cells, comprising contacting the adherent cells with cholera-toxin B conjugated to a dye or to an enzyme that generates a colored end-product upon contacting its substrate; and measuring light emitted by or absorbed by the dye or the colored end-product, wherein the light emitted or absorbed is used to quantitate the amount of gangliosides, e.g., GM1, in the population of adherent cells.

The invention further provides a ganglioside, e.g., GM1, produced by the methods of the invention.

The invention also relates to methods of treating diseases or disorders comprising administering the gangliosides, e.g., GM1, produced by the methods of the invention to a subject in need thereof.

BRIEF DESCRIPTION OF THE DRAWINGS/FIGURES

FIG. 1A Cells were obtained from the bone marrow of sheep with GM1 gangliosidosis ("affected sheep bone marrow cells") and expanded in culture. Control cells were maintained in standard culture media (upper panels). Induced cells labeled "48 h CLQ in NIM" (lower panels) were cultured in NIM and then treated for 48 hours with CLQ. Cells were stained with cholera toxin B conjugated to Alexa488 ("CTB-Alexa488"). Representative images are shown to demonstrate the extent of induction. Staining indicates presence of GM1. Cells in the lower panels that were treated show induction of GM1; staining is more prevalent and intense. Note the perinuclear staining in many cells.

FIG. 1B Cells obtained from the bone marrow of normal sheep were expanded in culture. Control cells were maintained in standard culture media (upper panels). Induced cells labeled "48 h CLQ in NIM" (lower panels) were cultured in NIM and then treated for 48 hours (h) with CLQ. Cells were stained with CTB-Alexa488. Images from different areas of the culture or different wells are shown to demonstrate the extent of induction. Staining indicates presence of GM1. Cells in the lower panels that were treated show induction of GM1; staining is more prevalent and intense. Note the perinuclear staining in many cells.

Figure 2:
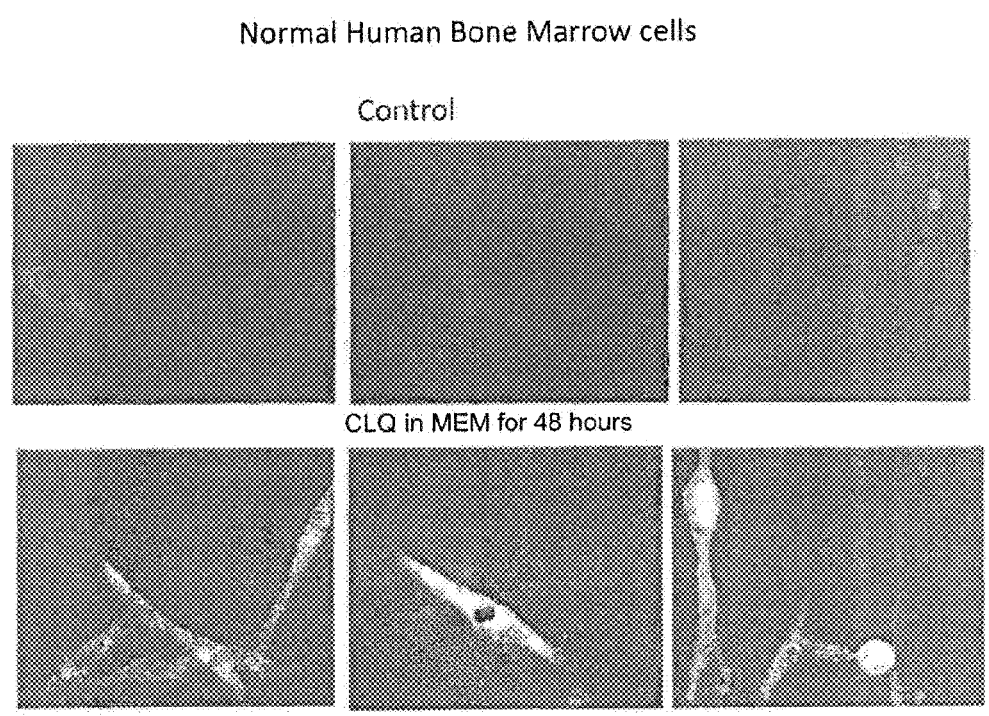

FIG. 2 Normal human adult bone marrow-derived stromal cells were plated in standard tissue culture flasks. Control cells were maintained in standard culture media (upper panels). Treated cells, labeled "CLQ," were treated with CLQ in Alpha MEM for 48 h (lower panels). Representative images are shown to demonstrate the extent of induction. Cells were stained with CTB-Alexa488. Staining indicates presence of GM1. GM1 signal in the treated cells (lower panels) is abundant and intense compared to control conditions.

Figure 3:
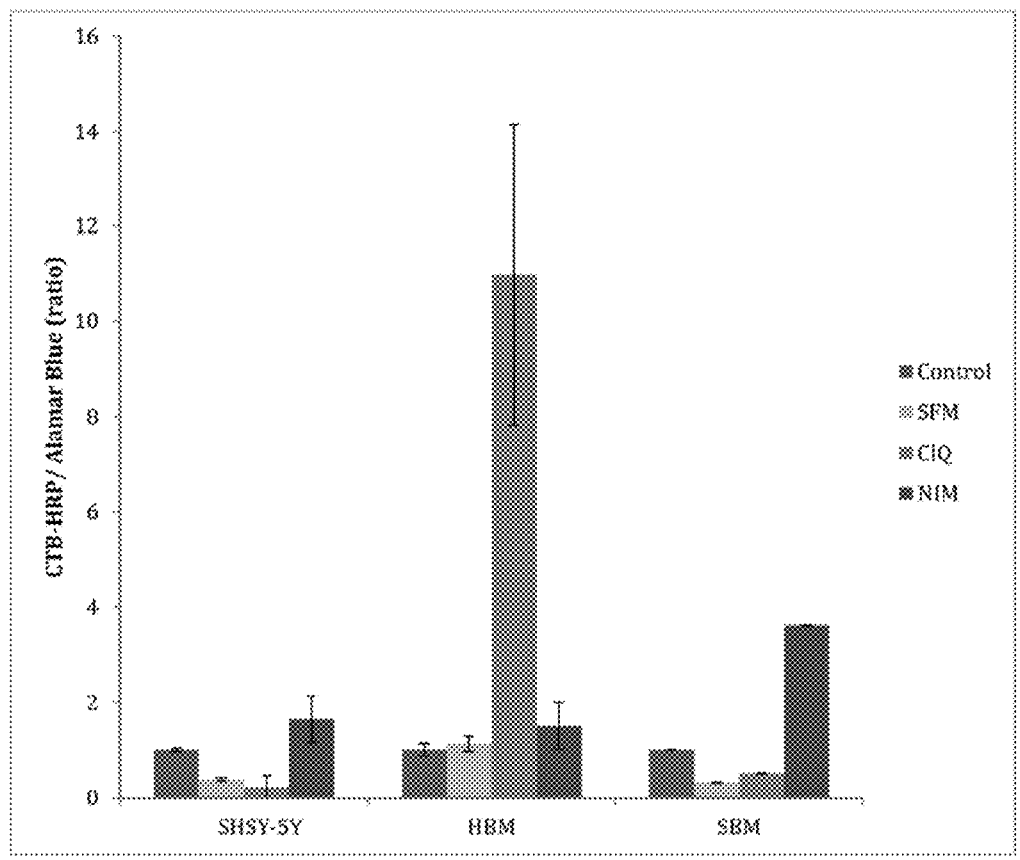

FIG. 3 A human neuroblastoma cell line, SHSY-5Y, sheep bone marrow cells ("SBM") and human bone marrow cells ("HBM") were each subjected to three different treatment regimens: (a) serum free medium ("SFM"), (b) NIM, or (c) CLQ. The amount of GM1 in each culture was determined using horseradish peroxidase ("HRP")-conjugated cholera toxin B ("CTB-HRP"). The amount of product generated by CTB-HRP that remained bound after incubation and washing was measured. The signal from Alamar Blue staining for each culture was also determined. The GM1 signal (as measured by CTB-HRP) was normalized to the number of cells in the well (as measured by Alamar Blue). The y axis of the bar graph indicates the extent of staining using CTB-HRP normalized for cell number, which indicates the amount of GM produced by each cell line for each treatment regime. Control cells were left untreated and were maintained in standard culture media. NIM and CLQ treatments showed the most robust induction of GM1.

Figure 4:
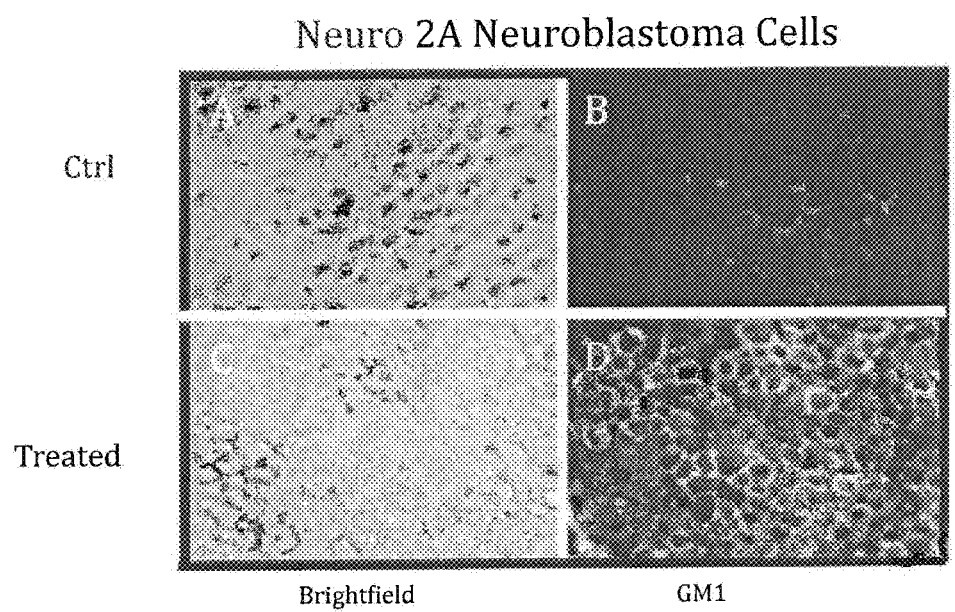

FIG. 4 Induction of GM1 in mouse neuro 2A neuroblastoma cells treated with neuraminidase. Neuro 2A cells were either maintained in standard culture media (Ctrl) or treated for 3 hours with neuraminidase. Treated cells show greater staining (see panel D), indicating higher accumulation of GM1 by the treated cells.

Figure 5:
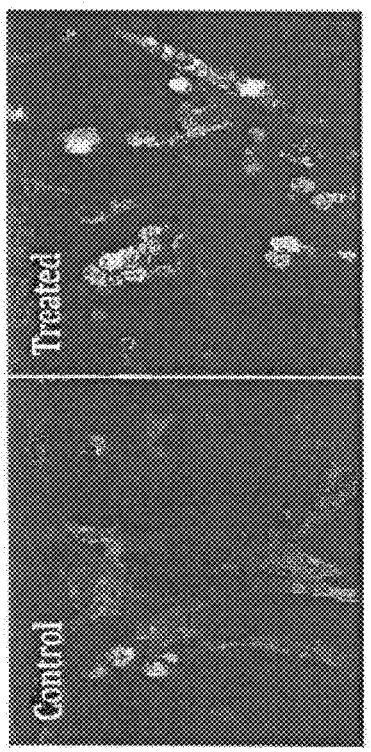

FIG. 5 Induction of GM1 in human adult bone marrow stromal cells (hABM-SC) with neuraminidase. hABM-SC were either maintained in standard culture media (control) or treated for 3 hours with neuraminidase (treated). Treated cells show greater staining intensity, indicating higher production of GM1 by the treated cells.

Figure 6:
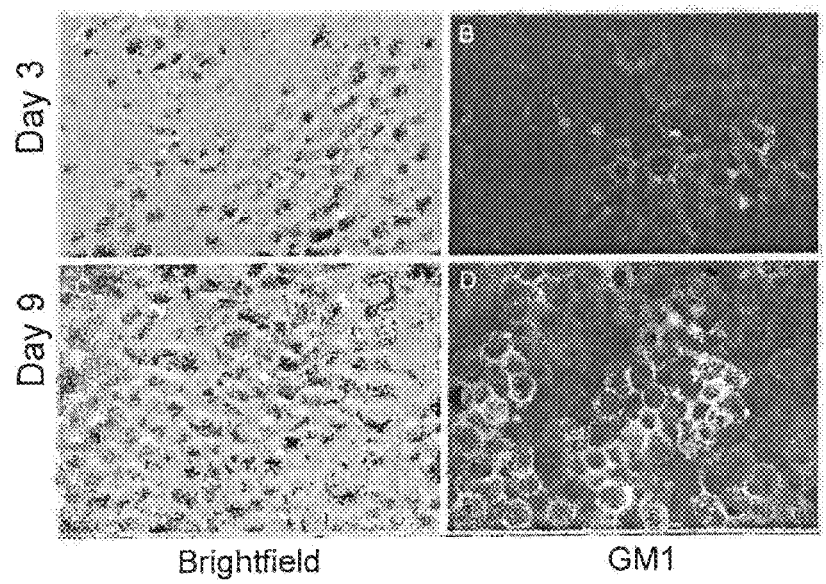

FIG. 6 Induction of GM1 in mouse neuro 2A neuroblastoma cells by high density-long term culture conditions. Mouse neuro 2A cells were plated at a high density. A subset of wells were fixed and stained for GM1 after 3 days in culture, while others were maintained for 9 days before fixation and staining for GM1. Greater staining of cells maintained for 9 days indicates greater GM1 production.

Figure 7:
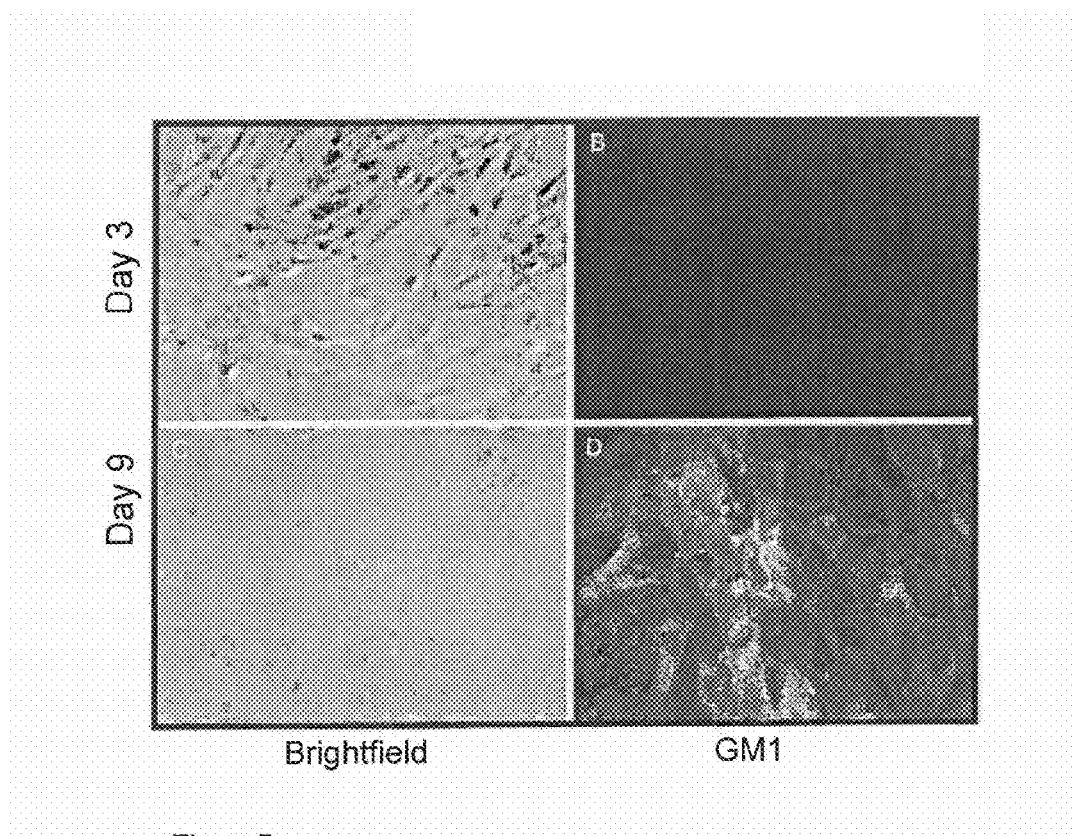

FIG. 7 Induction of GM1 in sheep brain-derived cells by high density-long term culture conditions. Sheep brain derived cells were plated at a high density. A subset of wells were fixed and stained for GM1 after 3 days in culture, while others were maintained for 9 days before fixation and staining for GM1. Brighter staining of cells maintained for 9 days indicates greater GM1 production.

Figure 8:
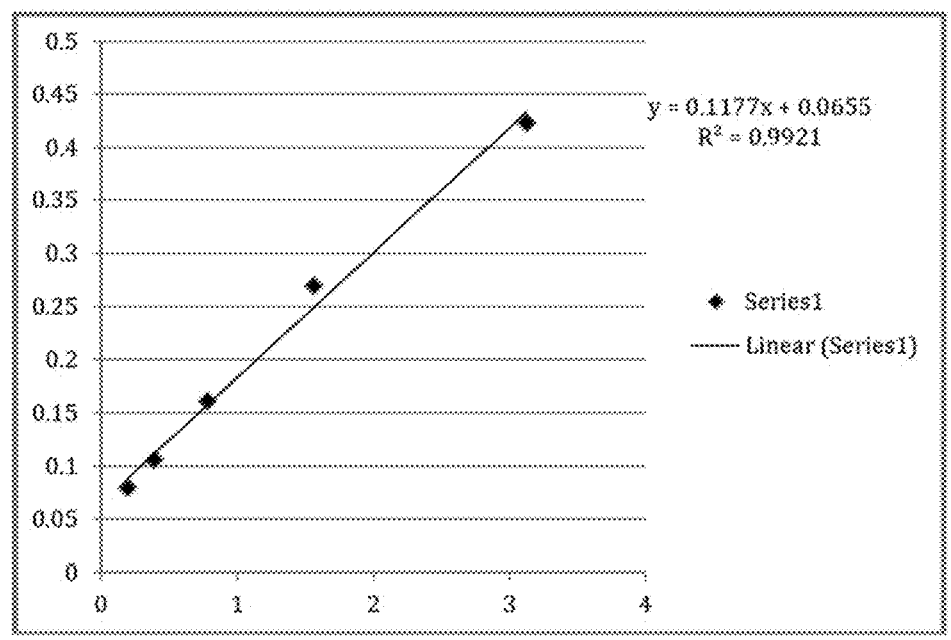

FIG. 8 Standard curve for plate based sheep GM1 quantification using CTB-HRP. An ELISA based plate was coated with various quantities of sheep GM1. Plates were washed, blocked and incubated with HRP conjugated-cholera toxin B. Substrate was added to generate a colored product which was measured using a plate reader. The signal intensity was correlated to the amount of GM1 added per well. This graph represents a standard curve generated by this method. GM1 levels can be quantified using this standard curve.

Figure 9:
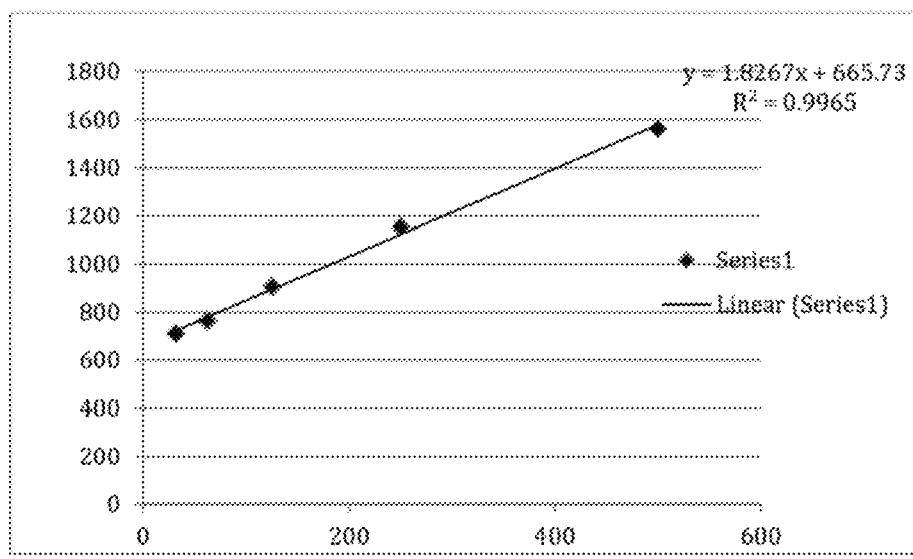

FIG. 9 Standard curve for plate based sheep GM1 quantification using CTB-Alexa488. An ELISA based plate was coated with various quantities of sheep GM1. Plates were washed, blocked, and incubated with CTB-Alexa488. The signal intensity was correlated to the amount of GM1 added per well. This graph represents a standard curve generated by this method. GM1 levels can be quantified using this standard curve.

Figure 10:
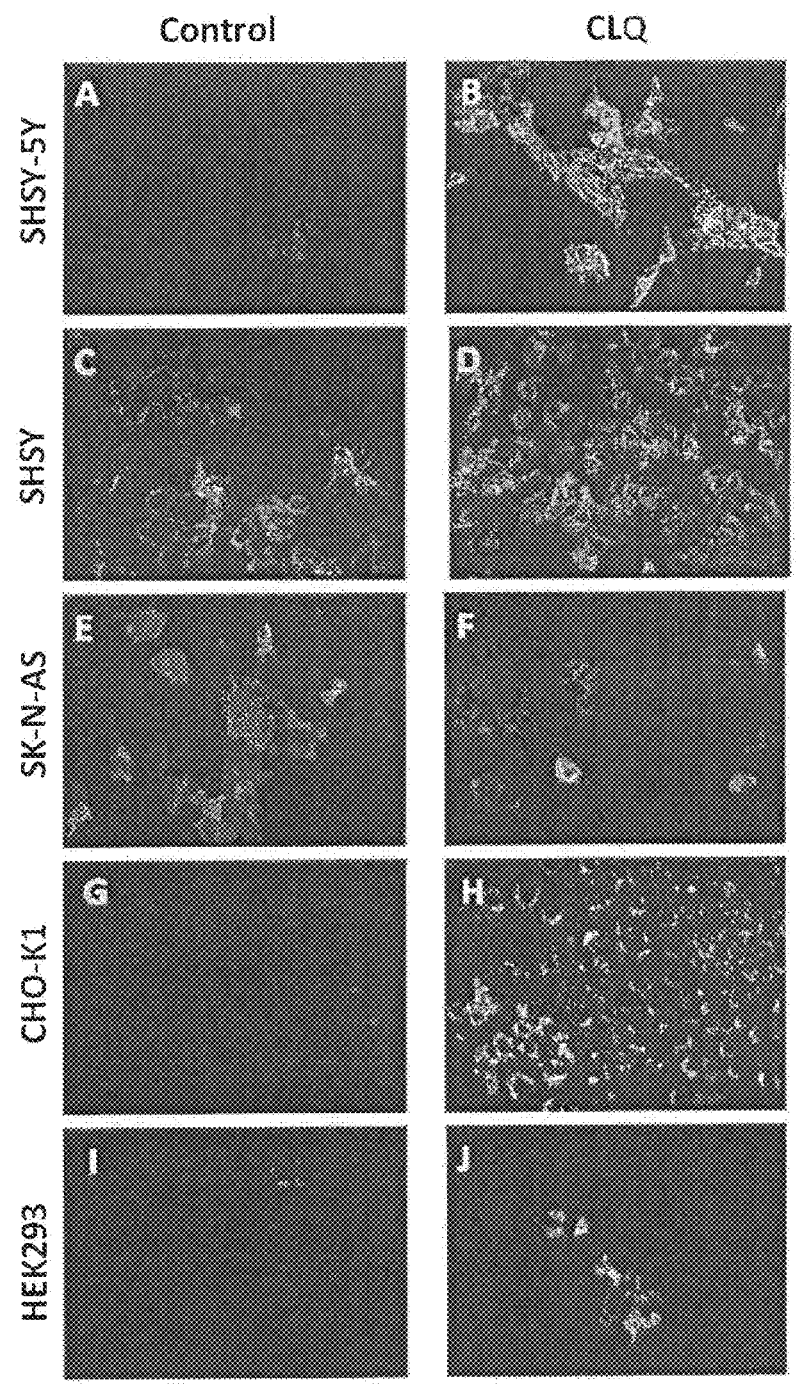

FIG. 10 Induction of GM1 in immortalized cell lines with CLQ. SHSY-5Y, SHSY-S, SK-N-AS, Chinese Hamster Ovary (CHO-K1), and Human Embryonic Kidney (HEK293) cells were plated in 24 well culture plates. Control cells were maintained in their respective standard culture media (FIG. 10, Panels A, C, E, G, I). Treated cells, labeled "CLQ," were treated with CLQ added to the standard culture media for 48-120 hours (FIG. 10, Panels B, D, F, H, J). Representative images are shown to demonstrate the extent of induction. Cells were stained with CTB-Alexa488. Staining indicates presence of GM1. GM1 signal in the treated cells is more abundant and intense compared to control conditions for all cell types, although the magnitude and distribution varied.

Figure 11:
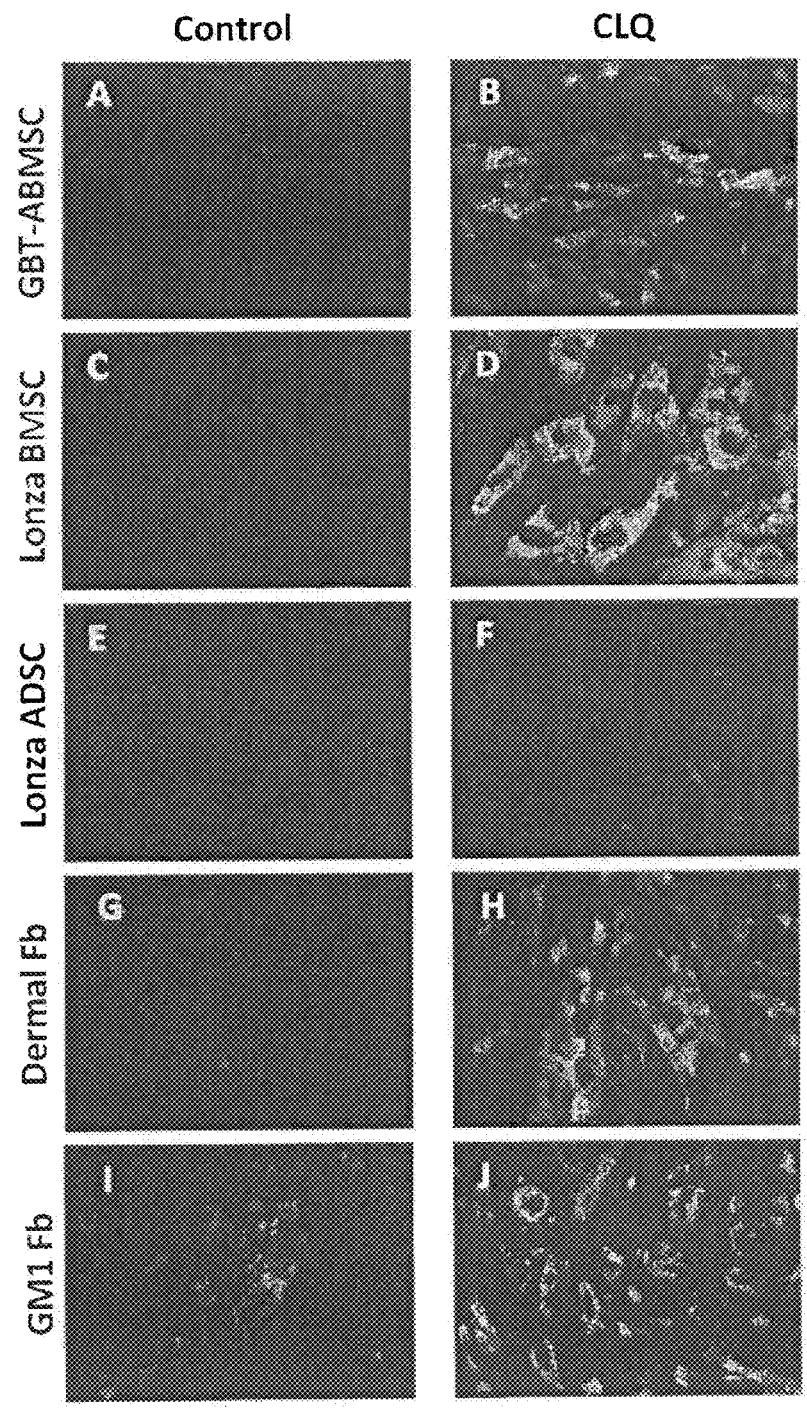

FIG. 11 Induction of GM1 in primary cell lines with CLQ. Garnet BioTherapeutics' adult bone marrow-derived stromal (GBT-ABMSC), bone marrow-derived stromal (Lonza BMSC), adipose-derived stromal (Lonza ADSC), dermal fibroblast (fb), and fibroblasts from subjects with GM1 gangliosidosis (GM1 fb) cells were plated in 24 well culture plates. Control cells were maintained in their respective standard culture media (FIG. 11, Panels A, C, E, G, I). Treated cells, labeled "CLQ", were treated with CLQ added to the standard culture media for 48-120 hours (FIG. 11, Panels B, D, F, H, I). Representative images are shown to demonstrate the extent of induction. Cells were stained with CTB-Alexa488. Staining indicates the presence of GM1. GM1 signal in the treated cells is more abundant and intense compared to control conditions for all cell types, although the magnitude and distribution varied.

DETAILED DESCRIPTION OF THE INVENTION

Introduction

The present invention provides methods of producing gangliosides, e.g., GM1, from cells in culture. Accordingly, the methods of the invention provide processes to enhance, or induce, the production of gangliosides, e.g., GM1, in cell culture using various manipulations. The following methods of the present invention will be described in detail below: (a) culturing cells with neuronal-induction media ("NIM"), followed by treatment with chloroquine ("CLQ"); (b) treating cultured cells with chloroquine alone, i.e., without initial treatment with NIM; (c) treating cultured cells with neuraminidase; (d) treating cultured cells with glucosamine; (e) biochemically modifying cells; (f) high density, long term culturing of cells without passaging to allow gangliosides, e.g., GM1, to accumulate in the cells. The types of cells appropriate for each method will also be discussed, as well as methods for isolating the cells before treatment with NIM/CLQ or CLQ. In certain non-exclusive embodiments, methods (a) and/or (c) and/or (d) and/or (e) and/or (f), and methods (b) and/or (c) and/or (d) and/or (e) and/or (f), are combined to further enhance ganglioside production in cultured cells. For example, cells first cultured with NIM/CLQ are subsequently cultured with neuraminidase, or cells treated with CLQ, and not NIM, are subsequently cultured with neuraminidase. In some embodiments, after chemical treatment, e.g., with NIM and/or CLQ and/or neuraminidase, the cells are subjected to high density, long term culturing without passaging to allow gangliosides, e.g., GM1, to accumulate in the chemically-treated cells. In other embodiments, any combination of treatments as disclosed in this application is possible.

The present invention also provides methods of quantifying the amount of gangliosides, e.g., GM1, in cell culture, also described in detail below.

The term "gangliosides," in one embodiment of the invention, encompasses all gangliosides. In another one embodiment of the invention, the ganglioside is GM1. In another embodiment of the invention, the ganglioside is GM2. In another embodiment of the invention, the ganglioside is GM3. In another embodiment of the invention, the ganglioside is GD1a. In another embodiment of the invention, the ganglioside is GD1b. In another embodiment of the invention, the ganglioside is GD3. In another embodiment of the invention, the ganglioside is GT1.

Ganglioside Production by Culturing in Neuronal-Induction Media, Followed by Treatment with CLQ In embodiments, cells are induced to accumulate gangliosides, e.g., GM1, by culturing in neuronal-induction media, followed by treatment with chloroquine. This combination treatment is abbreviated herein as "NIM/CLQ." In embodiments, the cells appropriate for use in this method are identified by their source, e.g., from the type of animal and the cell tissue source of the animal. Animal sources for use in the NIM/CLQ methods of the invention include, but are not limited to, human, sheep, rabbit, mouse, guinea pig, horse, pig, cat and dog. In embodiments of the invention, stromal cells, e.g., bone marrow and adipose-derived cells; and fibroblasts, e.g., fibroblasts from humans with GM1 gangliosidosis ("GM1 fibroblast") and dermal fibroblasts, from animal sources, including but not limited to the above recited animal sources can be used in the NIM/CLQ methods of the present invention. As used herein, the terms "bone marrow cells" and "bone marrow-derived cells" are used synonymously. In embodiments, the NIM/CLQ methods of the invention utilize the bone-marrow derived cells produced by the low density/low oxygen culture methods for isolating bone marrow from animal sources, described in detail below.

Additional cell types for use in the NIM/CLQ methods of the invention include immortalized cells. Other cell types include neuroblastoma cells isolated from animal sources including but not limited to the above-recited animal sources, including humans, and neuroblastoma cell lines (including but not limited to SHSY-5Y, SHSY-S, and SK-N-AS). Neuroblastomas are advantageous at least because these cells have a high growth rate.

In embodiments, each cell type used in the NIM/CLQ methods of the invention is cultured under the low density/low $O_2$ culture methods described in detail below prior to and/or during and/or after treatment.

In embodiments, the animal cell sources of the present invention are afflicted with GM1 gangliosidosis, GM2 gangliosidosis, or both, which is a lysosomal storage disorder characterized by the generalized accumulation of gangliosides. In embodiments, bone marrow cells and fibroblasts from human, sheep, cats or dogs afflicted with gangliosidosis are used in the NIM/CLQ methods of the present invention. In embodiments, the fibroblast is a GM1 fibroblast. In further embodiments, immortalized cells are used in the NIM/CLQ methods of the present invention, for example, CHO cells and human embryonic kidney cells, e.g., CHO-K1 cells and HEK293 cells. In other embodiments, neuroblastoma cells from mouse, sheep or humans and neuroblastoma cell lines (including but not limited to SHSY-5Y, SHSY-S, and SK-N-AS) are used in the NIM/CLQ methods of the present invention.

In embodiments, PC12 cells, HT22 cells, brain cells from a sheep afflicted with gangliosidosis, and fibroblast cells from a sheep afflicted with gangliosidosis are not used in the NIM/CLQ methods of the invention.

The term "neuronal induction media" refers to a solution for growing cells which, under the correct conditions, produces cells that assume one or more phenotypic features of a neuron. The degree of the neuronal phenotype induced by NIM depends on several factors, including, but not limited to, the starting cell type, the components of the media, the concentration of the NIM components, and the amount of time the cells are in contact with the NIM. In embodiments of the present invention, suitable neuronal induction media induces expression of gangliosides, e.g., GM1, in the cultured cells beyond the levels expressed by cells in standard culture media.

In embodiments, NIM comprises Neurobasal medium, B27 supplement with retinoic acid, epidermal growth factor and fibroblast growth factor. These NIM components are exemplary and additional NIM components are known in the art.

In embodiments, after isolation from their animal source, the cells for use in the NIM/CLQ methods of the invention are first cultured in standard culture media, e.g., Alpha-MEM growth medium supplemented with 10% fetal bovine serum ("FBS"); MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, for 2 to 24 hours, and preferably for 4 to 14 hours, and preferably for 12 hours. In embodiments, the cells are grown at standard cell seeding density, e.g., 2,000 to 20,000 cells/cm$^2$, and preferably 8,000 cells/cm$^2$, at approximately 37° C. in a humidified incubator under standard (5% $CO_2$) atmospheric conditions. After culturing in standard culture media, the media is replaced with NIM and the cells are cultured in NIM for between 2 and 24 hours, preferably between 6 and 18 hours, or preferably between 8 and 14 hours. Following treatment with NIM, CLQ is added to the flask to induce the NIM-cultured cells to further produce GM1. CLQ has been used to induce accumulation in PC12 (rat adrenal medulla tumor) cells. Yuyama et al., *FEBS Lett.* 580:6972-6976 (2006). However, CLQ only moderately increased GM1 levels in HT22 (mouse hippocampal) cells. Hirata et al., *J. Neurochem.* 119:839-847 (2011). In embodiments, while the cells are cultured in NIM, between 5 and 100 micromolar CLQ, between 20 and 60 micromolar CLQ, or between 40 and 50 micromolar CLQ is added to the culture flask. In embodiments, 50 micromolar CLQ is added to the culture flask. In other embodiments, 30 micromolar CLQ is added to the culture flask. In other embodiments, 25 micromolar CLQ is added to the culture flask. CLQ is contacted with the cultured cells for between 4 to 72 hours, preferably between 20 to 60 hours, and preferably between 48 to 60 hours. In embodiments CLQ is contacted with the cultured cells for 48 hours.

For particular cell types, such as sheep bone marrow cells, significant cell death results after NIM/CLQ treatment. In such embodiments, the dead cells in the flask are removed, and the remaining surviving cells are re-suspended in fresh growth medium, e.g., Alpha-MEM supplemented with 10% FBS, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, and cultured at approximately 37° C. in a humidified incubator under standard cell densities and 5% $CO_2$ atmosphere. In embodiments of the invention, following re-suspension in fresh growth medium, e.g., Alpha-MEM supplemented with 10% FBS, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS. The remaining surviving cells are again treated with CLQ to further induce ganglioside production under the conditions described above. If necessary, floating, dead cells are removed from the flask, and the remaining surviving cells are collected. In additional embodiments, a second treatment is not conducted, and the cells are harvested. The methods of the invention also provide that the amount of gangliosides, e.g., GM1, in the cell culture is quantified using the methods of the present invention either after treatment with NIM alone or after treatment with NIM and CLQ (before and after treatment). In embodiments, gangliosides, e.g., GM1, is isolated and purified using methods known in the art, such as those disclosed herein.

In additional embodiments of the invention, NIM/CLQ treatment increases the accumulation of all gangliosides. In embodiments of the invention, NIM/CLQ treatment increases the accumulation of GM1. In another embodiment of the invention, NIM/CLQ treatment of the invention increases the accumulation of GM2. In another embodiment of the invention, NIM/CLQ treatment of the invention increases the accumulation of GM3. In another embodiment of the invention, NIM/CLQ treatment of the invention increases the accumulation of GD1a. In another embodiment of the invention, NIM/CLQ treatment of the invention increases the accumulation of GD1b. In another embodiment of the invention, NIM/CLQ treatment of the invention increases the accumulation of GD3. In another embodiment of the invention, NIM/CLQ treatment of the invention increases the accumulation of GT1.

In another embodiment, NIM/CLQ treatment increases the accumulation of two or more gangliosides. In a further embodiment, NIM/CLQ treatment increases the accumulation of three or more gangliosides. In a further embodiment, NIM/CLQ treatment increases the accumulation of four or more gangliosides. In a further embodiment, NIM/CLQ treatment increases the accumulation of five or more gangliosides.

In additional embodiments of the invention, NIM/CLQ treatment results in 10 to 200 percent or about 10 to 200 percent more ganglioside accumulation in a cell compared with a cell that has not been treated with NIM/CLQ. In another embodiment of the invention, NIM/CLQ treatment results in 15 to 125 percent or about 15 to 125 percent more ganglioside accumulation than a cell that has not been treated with NIM/CLQ. In another embodiment of the invention, NIM/CLQ treatment results in 30 to 100 percent or about 30 to 100 percent more ganglioside accumulation than a cell that has not been treated with NIM/CLQ. In another embodiment of the invention, NIM/CLQ treatment results in 60 to 80 percent or about 60 to 80 percent more ganglioside accumulation than a cell that has not been treated with NIM/CLQ. In another embodiment of the invention, NIM/CLQ treatment results in 15, 19, 28, 63, 65, 83, 104, and 119 percent or about 15, 19, 28, 63, 65, 83, 104, and 119 percent more ganglioside accumulation than a cell that has not been treated with NIM/CLQ. In another embodiment of the invention, NIM/CLQ treatment results in 65 percent more ganglioside accumulation than a cell that has not been treated with NIM/CLQ.

The invention further provides a ganglioside produced by the NIM/CLQ methods of the invention.

The invention further provides methods of treating a subject in need of treatment, by administering the ganglioside, e.g., GM1, made by the NIM/CLQ methods of the invention. In embodiments, a subject having neuronal injury is treated by administering a ganglioside, e.g., GM1, produced by the NIM/CLQ methods of the invention. In embodiments, a subject having Parkinson's disease is treated by administering a ganglioside, e.g., GM1, produced by the NIM/CLQ methods of the invention. In embodiments, a subject having Alzheimer's disease is treated by administering a ganglioside, e.g., GM1, produced by the NIM/CLQ methods of the invention. In embodiments, a subject who has had or is having a stroke is treated by administering a ganglioside, e.g., GM1, produced by the NIM/CLQ methods of the invention. In embodiments, a subject having Guillain-Barré syndrome is treated by administering a ganglioside, e.g., GM1, produced by the NIM/CLQ methods of the invention. In embodiments, a subject having cancer is treated by administering a ganglioside, e.g., GM1, produced by the NIM/CLQ methods of the invention.

In an exemplary embodiment, gangliosides, e.g., GM1, accumulate in normal sheep bone marrow-derived cells and gangliosidosis-affected sheep bone marrow-derived cells. In exemplary embodiments, sheep-bone marrow derived cells are obtained by the low-oxygen, low-density methods described below. Such cells are then cultured in Alpha-MEM growth medium, with 10% FBS, at a density of 8,000 cells/$cm^2$. After approximately 12 hours, the medium is replaced with 30 ml NIM, which comprises neurobasal medium, B27 supplement with retinoic acid, EGF (25 micrograms/ml) and FGF (10 nanograms/ml). After approximately 10 hours, 50 micromolar CLQ is added to the flask. About 70% cell death is observed on the third day. The floating cells are removed by rinsing with PBS. Surviving cells are collected by trypsinization, spun down, re-suspended in fresh growth medium and seeded in a new flask at 8,000 cells/$cm^2$. An aliquot is removed and plated in a 24-well plate for confirming ganglioside, e.g., GM1, induction by staining with appropriate stains, e.g., CTB-Alexa488. The surviving cells are allowed to expand in the flask for 2 days and the cells are harvested. In embodiments, the surviving cells can be treated for a second time with 50 micromolar CLQ for 24 hours before harvesting. After cell harvest, gangliosides, e.g., GM1, can be isolated and purified using the methods disclosed below.

Ganglioside Production by Treatment with Chloroquine

In additional embodiments, ganglioside, e.g., GM1, accumulation is induced in cells using chloroquine treatment without first culturing with neuronal-induction media. This method is also termed "CLQ treatment method" or "CLQ treatment" herein. In embodiments, animal sources of cells for use in the method of CLQ treatment include, but are not limited to, human, rabbit, mouse, guinea pig, horse, pig, cat and dog. In embodiments of the invention, fibroblasts and stromal cells, e.g., bone marrow and adipose-derived cells; and fibroblasts, e.g., GM1 fibroblast and dermal fibroblasts, from animal sources, including but not limited to the above recited animal sources can be used in the CLQ methods of the present invention. Exemplary methods for isolating cells from animal sources are described in detail below. In embodiments, cells produced by the low density/low oxygen culture methods described below are treated with CLQ to induce production of gangliosides, e.g., GM1. In embodiments, human bone marrow cells produced by the low density/low oxygen culture methods described below are treated with CLQ to induce production of gangliosides, e.g., GM1.

In additional embodiments of the CLQ treatment methods of the invention, immortalized cells, for example, CHO cells and human embryonic kidney cells, e.g., CHO-K1 cells and HEK293 cells, are used in the CLQ methods of this invention. In further embodiments, neuroblastoma cells isolated from animal sources, including but not limited to, the above-recited animal sources, including humans, and neuroblastoma cell lines (including but not limited to SHSY-5Y, SHSY-S, and SK-N-AS) are used in the CLQ methods of the invention. In further embodiments, the cells for use in the CLQ methods of the present invention are derived from animals afflicted with gangliosidosis, e.g., humans, cats or dogs afflicted with GM1 gangliosidosis, GM2 gangliosidosis, or both. In further embodiments, bone marrow cells and fibroblasts from human, sheep, cats or dogs afflicted with gangliosidosis are used in the CLQ methods of the present invention. In embodiments, the fibroblast is a GM1 fibroblast.

In embodiments, each cell type used in the CLQ methods of the invention is cultured under the low density/low $O_2$ culture methods described in detail below prior to and/or during and/or after treatment.

In embodiments, PC12 cells, HT22 cells, brain cells from a sheep afflicted with gangliosidosis, and fibroblast cells from a sheep afflicted with gangliosidosis are not used in the CLQ methods of the invention.

In embodiments, cells from the desired source are cultured in standard growth medium, e.g., Alpha-MEM supplemented with 10% FBS, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS: F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, under standard seeding density, e.g., 2,000 to 20,000 cells/cm$^2$, and preferably 8,000 cells/cm$^2$, at 37° C. under 5% $CO_2$ atmospheric conditions. In embodiments, the cells are cultured for 2 to 48 hours, and preferably for 8 to 36 hours, and preferably for 24 hours. After culturing, the culture media is optionally replaced with standard medium supplemented with serum; in embodiments, the amount of serum is less than the amount of serum in the previous culture media. CLQ is added to the culture media. In embodiments, between 5 and 100 micromolar CLQ, between 25 and 75 micromolar CLQ, or between 40 and 50 micromolar CLQ is added to the culture flask. In embodiments, 50 micromolar CLQ is added to the culture flask. In other embodiments, 30 micromolar CLQ is added to the culture flask. In other embodiments, 25 micromolar CLQ is added to the culture flask. The CLQ is contacted with the cultured cells for between 2 to 72 hours, preferably between 20 to 60 hours, and preferably between 30 to 50 hours. In embodiments, the cells are incubated with CLQ for 48 hours and harvested. In an additional embodiment, the amount of gangliosides, e.g., GM1, in the cell culture is quantified using the methods of the present invention. The gangliosides, e.g., GM1, can subsequently be isolated and purified from the cell culture using standard methods, such as those described below.

In an exemplary embodiment, human bone-marrow derived cells cultured in Alpha-MEM growth medium (with 10% FBS) are seeded at a density of 8,000 cells/cm$^2$. After about 24 hours, the medium is replaced with reduced serum Alpha-MEM (with 1% FBS) and 50 micromolar CLQ is added. The cells are incubated for about 48 hours before harvesting.

In additional embodiments of the invention, CLQ treatment increases the accumulation of all gangliosides. In one embodiment of the invention, CLQ treatment increases the accumulation of GM1. In another embodiment of the invention, CLQ treatment of the invention increases the accumulation of GM2. In another embodiment of the invention, CLQ treatment of the invention increases the accumulation of GM3. In another embodiment of the invention, CLQ treatment of the invention increases the accumulation of GD1a. In another embodiment of the invention, CLQ treatment of the invention increases the accumulation of GD1b. In another embodiment of the invention, CLQ treatment of the invention increases the accumulation of GD3. In another embodiment of the invention, CLQ treatment of the invention increases the accumulation of GT1.

In another embodiment, CLQ treatment increases the accumulation of two or more gangliosides. In a further embodiment, CLQ treatment increases the accumulation of three or more gangliosides. In a further embodiment, CLQ treatment increases the accumulation of four or more gangliosides. In a further embodiment, CLQ treatment increases the accumulation of five or more gangliosides.

In additional embodiments of the invention, CLQ treatment results in 10 to 200 percent or about 10 to 200 percent more ganglioside accumulation in a cell compared with a cell that has not been treated with chloroquine. In another embodiment of the invention, CLQ treatment results in 15 to 125 percent or about 15 to 125 percent more ganglioside accumulation than a cell that has not been treated with chloroquine. In another embodiment of the invention, CLQ treatment results in 30 to 100 percent or about 30 to 100 percent more ganglioside accumulation than a cell that has not been treated with chloroquine. In another embodiment of the invention, CLQ treatment results in 60 to 80 percent or about 60 to 80 percent more ganglioside accumulation than a cell that has not been treated with chloroquine. In another embodiment of the invention, CLQ treatment results in 15, 19, 28, 63, 65, 83, 104, and 119 percent or about 15, 19, 28, 63, 65, 83, 104, and 119 percent more ganglioside accumulation than a cell that has not been treated with chloroquine. In another embodiment of the invention, CLQ treatment results in 65 percent more ganglioside accumulation than a cell that has not been treated with chloroquine.

The invention further provides a ganglioside produced by the CLQ treatment methods of the invention.

The invention further provides methods of treating a subject having a disease or disorder in need of such treatment by administering a ganglioside, e.g., GM1, produced by the CLQ treatment methods of the invention. In embodiments, a subject having neuronal injury is treated by administering a ganglioside, e.g., GM1, produced by the CLQ treatment methods of the invention. In embodiments, a subject having Parkinson's disease is treated by administering a ganglioside, e.g., GM1, produced by the CLQ treatment methods of the invention. In embodiments, a subject having Alzheimer's disease is treated by administering a ganglioside, e.g., GM1, produced by the CLQ treatment methods of the invention. In embodiments, a subject who has had or is having a stroke is treated by administering a ganglioside, e.g., GM1, produced by the CLQ treatment methods of the invention. In embodiments, a subject having Guillain-Barré syndrome is treated by administering a ganglioside, e.g., GM1, produced by the CLQ treatment methods of the invention. In embodiments, a subject having cancer is treated by administering a ganglioside, e.g., GM1, produced by the CLQ treatment methods of the invention.

Ganglioside Production by Treatment with Neuraminidase

In additional embodiments, excess ganglioside, e.g., GM1, production is induced in cells using neuraminidase, either alone or with CLQ. The combination of treatment with neuraminidase and chloroquine is abbreviated herein as "neuraminidase/CLQ." Neuraminidase is a sialidase enzyme that converts the major brain complex gangliosides, e.g., GD1a, GD1b, and GT1b, to GM1 in intact cells. In embodiments, sources for cells for use in the method of neuraminidase treatment include, but are not limited to, human, sheep, rabbit, mouse, guinea pig, horse, pig, cat and dog. In embodiments of the invention, cells isolated from animal sources, including but not limited to the animal sources recited above, such as stromal cells, e.g., bone marrow and adipose-derived cells; and fibroblasts, e.g., GM1 fibroblast and dermal fibroblasts, can be used in the neuraminidase and neuraminidase/CLQ methods of the present invention. In other embodiments of the invention, bone marrow cells isolated from each of these animal sources can be used in the neuraminidase and neuraminidase/CLQ methods of the present invention. Exemplary methods for isolating bone marrow from animal sources are described in detail below. In embodiments, cells produced by the low density/low oxygen culture methods described below are treated with neuraminidase and neuraminidase/CLQ to induce production of gangliosides, e.g., GM1. In embodiments, human bone marrow cells produced by the low density/low oxygen culture methods described below are treated with neuraminidase and neuraminidase/CLQ to induce production of gangliosides, e.g., GM1.

In additional embodiments of the invention, immortalized cells, for example, CHO cells and human embryonic kidney cells, e.g., CHO-K1 cells and HEK293 cells, are used in the neuraminidase and neuraminidase/CLQ methods of the invention. In further embodiments, neuroblastoma cells isolated from animal sources, including but not limited to the above-recited animal sources, including humans, and neuroblastoma cell lines (including but not limited to SHSY-5Y, SHSY-S, and SK-N-AS) are used in the neuraminidase and neuraminidase/CLQ methods of the invention. In further embodiments, the cells for use in the neuraminidase and neuraminidase/CLQ methods of the present invention are derived from animals afflicted with gangliosidosis e.g., humans, cats or dogs afflicted with GM1 gangliosidosis, GM2 gangliosidosis, or both. In further embodiments, bone marrow cells and fibroblasts from human, sheep, cats or dogs afflicted with gangliosidosis are used in the neuraminidase and neuraminidase/CLQ methods of the present invention. In embodiments, the fibroblast is a GM1 fibroblast.

In embodiments, each cell type used in the neuraminidase and neuraminidase/CLQ methods of the invention is cultured under the low density/low $O_2$ culture methods described in detail below prior to and/or during and/or after treatment.

In embodiments, PC12 cells, HT22 cells, brain cells from a sheep afflicted with gangliosidosis, and fibroblast cells from a sheep afflicted with gangliosidosis are not used in the neuraminidase and neuraminidase/CLQ methods of the invention.

In embodiments, cells derived from the desired source are cultured in standard growth medium, e.g., Alpha-MEM supplemented with serum, e.g., 10% FBS, additionally supplemented with 1 to 4 mM glutamine under standard seeding density, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, e.g., 2,000 to 20,000 cells/cm$^2$, and preferably 8,000 cells/cm$^2$, at 37° C. in a humidified incubator under standard (5% $CO_2$) atmospheric conditions. Neuraminidase is added to the culture media and the cells are treated with neuraminidase for 1 to 5 hours, preferably 2 to 4 hours, and preferably 3 hours. In embodiments, between 1 and 5 units/ml of neuraminidase are added to the culture media, and preferably 1 unit/ml. In an additional embodiment, the amount of gangliosides, e.g., GM1, in the cell culture is quantified using the methods of the present invention. The gangliosides, e.g., GM1, can also be isolated and purified from the cell culture using standard methods, such as those described below.

In additional embodiments of the invention, the neuraminidase and neuraminidase/CLQ methods increase the accumulation of all gangliosides. In one embodiment of the invention, the neuraminidase and neuraminidase/CLQ methods increase the accumulation of GM1. In another embodiment of the invention, the neuraminidase and neuraminidase/CLQ methods of the invention increase the accumulation of GM2. In another embodiment of the invention, the neuraminidase and neuraminidase/CLQ methods of the invention increase the accumulation of GM3. In another embodiment of the invention, the neuraminidase and neuraminidase/CLQ methods of the invention increase the accumulation of GD1a. In another embodiment of the invention, the neuraminidase and neuraminidase/CLQ methods of the invention increase the accumulation of GD1b. In another embodiment of the invention, the neuraminidase and neuraminidase/CLQ methods of the invention increase the accumulation of GD3. In another embodiment of the invention, the neuraminidase and neuraminidase/CLQ methods of the invention increase the accumulation of GT1.

In another embodiment, the neuraminidase and neuraminidase/CLQ methods increases the accumulation of two or more gangliosides. In a further embodiment, the neuraminidase and neuraminidase/CLQ methods increases the accumulation of three or more gangliosides. In a further embodiment, the neuraminidase and neuraminidase/CLQ methods increases the accumulation of four or more gangliosides. In a further embodiment, the neuraminidase and neuraminidase/CLQ methods increases the accumulation of five or more gangliosides.

In additional embodiments of the invention, the neuraminidase and neuraminidase/CLQ methods results in 10 to 200 percent or about 10 to 200 percent more ganglioside accumulation in a cell compared with a cell that has not been treated with neuraminidase and neuraminidase/CLQ. In another embodiment of the invention, the neuraminidase and neuraminidase/CLQ methods results in 15 to 125 percent or about 15 to 125 percent more ganglioside accumulation than a cell that has not been treated with neuraminidase and neuraminidase/CLQ. In another embodiment of the invention, the neuraminidase and neuraminidase/CLQ methods results in 15, 19, 28, 63, 65, 83, 104, and 119 percent or about 15, 19, 28, 63, 65, 83, 104, and 119 percent more ganglioside accumulation than a cell that has not been treated with neuraminidase and neuraminidase/CLQ. In another embodiment of the invention, the neuraminidase and neuraminidase/CLQ methods results in 65 percent more ganglioside accumulation than a cell that has not been treated with neuraminidase and neuraminidase/CLQ.

The invention further provides a ganglioside produced by the neuraminidase and neuraminidase/CLQ treatment methods of the invention.

The invention further provides methods of treating a subject having a disease or disorder in need of such treatment by administering a ganglioside, e.g., GM1, produced by the neuraminidase and neuraminidase/CLQ methods of the invention. In embodiments, a subject having neuronal injury is treated by administering a ganglioside, e.g., GM1, produced by the neuraminidase and neuraminidase/CLQ methods of the invention. In embodiments, a subject having Parkinson's disease is treated by administering a ganglioside, e.g., GM1, produced by the neuraminidase and neuraminidase/CLQ methods of the invention. In embodiments, a subject having Alzheimer's disease is treated by administering a ganglioside, e.g., GM1, produced by the neuraminidase and neuraminidase/CLQ methods of the invention. In embodiments, a subject who has had or is having a stroke is treated by administering a ganglioside, e.g., GM1, produced by the neuraminidase and neuraminidase/CLQ methods of the invention. In embodiments, a subject having Guillain-Barré syndrome is treated by administering a ganglioside, e.g., GM1, produced by the neuraminidase and neuraminidase/CLQ methods of the invention. In embodiments, a subject having cancer is treated by administering a ganglioside, e.g., GM1, produced by the neuraminidase and neuraminidase/CLQ methods of the invention.

Ganglioside Production by Treatment with Glucosamine

In additional embodiments, excess ganglioside, e.g., GM1, production is induced in cells using glucosamine either alone or with CLQ. The combination of treatment with glucosamine with chloroquine is abbreviated herein as "glucosamine/CLQ." Under certain conditions, glucosamine treatment increases ganglioside levels, for example, GM1 and GM2, as disclosed by Masson et al. *Biochem. J.* 388:537-544 (2005), herein incorporated by reference in its entirety. Sources for cells for use in the method of glucosamine and glucosamine/CLQ methods include, but are not limited to, human, sheep, rabbit, mouse, guinea pig, horse, pig, cat and dog. In embodiments of the invention, fibroblasts and stromal cells, e.g., bone marrow and adipose-derived cells; and fibroblasts, e.g., GM1 fibroblast and dermal fibroblasts, from animal sources, including but not limited to the above recited animal sources can be used in the glucosamine and glucosamine/CLQ methods of the present invention. Exemplary methods for isolating cells from animal sources are described in detail below. In embodiments, cells produced by the low density/low oxygen culture methods described below are treated with glucosamine and glucosamine/CLQ to induce production of gangliosides, e.g., GM1. In embodiments, human bone marrow cells produced by the low density/low oxygen culture methods described below are treated with glucosamine and glucosamine/CLQ to induce production of gangliosides, e.g., GM1.

In additional embodiments of the invention, immortalized cells, for example, CHO cells and human embryonic kidney cells, e.g., CHO-K1 cells and HEK293 cells, are used in the glucosamine and glucosamine/CLQ methods of the invention. In further embodiments, neuroblastoma cells isolated from animal sources, including but not limited to, the above-recited animal sources, including humans, and neuroblastoma cell lines (including but not limited to SHSY-5Y, SHSY-S, and SK-N-AS) are used in the glucosamine and glucosamine/CLQ methods of the invention. In further embodiments, the cells for use in the glucosamine and glucosamine/CLQ methods of the present invention are derived from animals afflicted with gangliosidosis e.g., humans, cats or dogs afflicted with GM1 gangliosidosis, GM2 gangliosidosis, or both. In further embodiments, bone marrow cells and fibroblasts from human, sheep, cats or dogs afflicted with gangliosidosis are used in the glucosamine and glucosamine/CLQ methods of the present invention. In embodiments, the fibroblast is a GM1 fibroblast.

In embodiments, each cell type used in the glucosamine and glucosamine/CLQ methods of the invention is cultured with the low density/low $O_2$ culture methods described in detail below prior to and/or during and/or after treatment.

In embodiments, PC12 cells, HT22 cells, brain cells from a sheep afflicted with gangliosidosis, and fibroblast cells from a sheep afflicted with gangliosidosis are not used in the glucosamine and glucosamine/CLQ methods of the invention.

In embodiments, cells derived from the desired source are cultured in standard growth medium, e.g., Alpha-MEM supplemented with serum, e.g., 10% FBS, additionally supplemented with 1 to 4 mM glutamine under standard seeding density, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, e.g., 2,000 to 20,000 cells/cm$^2$, and preferably 8,000 cells/cm$^2$, at 37° C. in a humidified incubator under standard (5% $CO_2$) atmospheric conditions. Glucosamine is added to the media and cultured as disclosed by Masson et al. *Biochem. J.* 388:537-544 (2005). In an additional embodiment, the amount of gangliosides, e.g., GM1, in the cell culture is quantified using the methods of the present invention. The gangliosides, e.g., GM1, can also be isolated and purified from the cell culture using standard methods, such as those described below.

In additional embodiments of the invention, glucosamine and glucosamine/CLQ treatment increases the accumulation of all gangliosides. In one embodiment of the invention, glucosamine and glucosamine/CLQ treatment increases the accumulation of GM1. In another embodiment of the invention, glucosamine and glucosamine/CLQ treatment of the invention increases the accumulation of GM2. In another embodiment of the invention, glucosamine and glucosamine/CLQ treatment of the invention increases the accumulation of GM3. In another embodiment of the invention, glucosamine and glucosamine/CLQ treatment of the invention increases the accumulation of GD1a. In another embodiment of the invention, glucosamine and glucosamine/CLQ treatment of the invention increases the accumulation of GD1b. In another embodiment of the invention, glucosamine and glucosamine/CLQ treatment of the invention increases the accumulation of GD3. In another embodiment of the invention, glucosamine and glucosamine/CLQ treatment of the invention increases the accumulation of GT1.

In another embodiment, glucosamine and glucosamine/CLQ treatment increases the accumulation of two or more gangliosides. In a further embodiment, glucosamine and glucosamine/CLQ treatment increases the accumulation of three or more gangliosides. In a further embodiment, glucosamine and glucosamine/CLQ treatment increases the accumulation of four or more gangliosides. In a further embodiment, glucosamine and glucosamine/CLQ treatment increases the accumulation of five or more gangliosides.

In additional embodiments of the invention, glucosamine and glucosamine/CLQ treatment results in 10 to 200 percent or about 10 to 200 percent more ganglioside accumulation in a cell compared with a cell that has not been treated with glucosamine and glucosamine/CLQ. In another embodiment of the invention, glucosamine and glucosamine/CLQ treatment results in 15 to 125 percent or about 15 to 125 percent more ganglioside accumulation than a cell that has not been treated with glucosamine and glucosamine/CLQ. In another embodiment of the invention, glucosamine and glucosamine/CLQ treatment results in 30 to 100 percent or about 30 to 100 percent more ganglioside accumulation than a cell that has not been treated with glucosamine and glucosamine/CLQ. In another embodiment of the invention, glucosamine and glucosamine/CLQ treatment results in 60 to 80 percent or about 60 to 80 percent more ganglioside accumulation than a cell that has not been treated with glucosamine and glucosamine/CLQ. In another embodiment of the invention, glucosamine and glucosamine/CLQ treatment results in 15, 19, 28, 63, 65, 83, 104, and 119 percent or about 15, 19, 28, 63, 65, 83, 104, and 119 percent more ganglioside accumulation than a cell that has not been treated with glucosamine and glucosamine/CLQ. In another embodiment of the invention, glucosamine and glucosamine/CLQ treatment results in 65 percent more ganglioside accumulation than a cell that has not been treated with glucosamine and glucosamine/CLQ.

The invention further provides a ganglioside produced by the glucosamine and glucosamine/CLQ methods of the invention.

The invention further provides methods of treating a subject having a disease or disorder in need of such treatment by administering a ganglioside, e.g., GM1, produced by the glucosamine and glucosamine/CLQ methods of the invention. In embodiments, a subject having neuronal injury is treated by administering a ganglioside, e.g., GM1, produced by the glucosamine and glucosamine/CLQ methods of the invention. In embodiments, a subject having Parkinson's disease is treated by administering a ganglioside, e.g., GM1, produced by the glucosamine and glucosamine/CLQ methods of the invention. In embodiments, a subject having Alzheimer's disease is treated by administering a ganglioside, e.g., GM1, produced by the glucosamine and glucosamine/CLQ methods of the invention. In embodiments, a subject who has had or is having a stroke is treated by administering a ganglioside, e.g., GM1, produced by the glucosamine and glucosamine/CLQ methods of the invention. In embodiments, a subject having Guillain-Barré syndrome is treated by administering a ganglioside, e.g., GM1, produced by the glucosamine and glucosamine/CLQ methods of the invention. In embodiments, a subject having cancer is treated by administering a ganglioside, e.g., GM1, produced by the glucosamine and glucosamine/CLQ methods of the invention.

Ganglioside Production by Biochemical Manipulation

In additional embodiments, excess ganglioside, e.g., GM1, production is induced in cells by biochemical manipulation either alone or in combination with CLQ. The combination of biochemical manipulation with chloroquine treatment is abbreviated herein as "biochemical manipulation/CLQ." Under certain conditions, alteration of certain enzyme levels increases ganglioside levels, causing disease. GM1 gangliosidosis is caused by an elevated level of GM1 caused by a deficiency of the lysosomal β-galactosidase enzyme, which hydrolyses the terminal β-galactosyl residues from GM1 ganglioside, glycoproteins and glycosaminoglycans. Christie, "Ganglioside," The AOCS Lipid Library, last updated Jul. 23, 2012. Additionally, GM2 gangliosidosis is caused by insufficient activity of a specific enzyme, β-Nacetylhexosaminidase, which catalyzes the degradation of gangliosides. Id. Furthermore, many of the enzymes that convert gangliosides from one form into another are known. Thus, altering expression and/or activity of these enzymes can increase the production of a particular ganglioside. Known methods such as, but not limited to knockdown, e.g., knockdown, transfection, e.g., transient or stable, chemical inhibition, e.g., small molecule or biologics, and antibodies, can be used for the methods of the invention. Sources for cells for use in the biochemical manipulation and biochemical manipulation/CLQ method include, but are not limited to, human, sheep, rabbit, mouse, guinea pig, horse, pig, cat and dog. In embodiments of the invention, fibroblasts and stromal cells, e.g., bone marrow and adipose-derived cells; and fibroblasts, e.g., GM1 fibroblast and dermal fibroblasts, from animal sources, including but not limited to the above recited animal sources can be used in the biochemical manipulation and biochemical manipulation/CLQ methods of the present invention. Exemplary methods for isolating cells from animal sources are described in detail below. In embodiments, cells produced by the low density/low oxygen culture methods described below are used in the biochemical manipulation and biochemical manipulation/CLQ methods to induce production of gangliosides, e.g., GM1. In embodiments, human bone marrow cells produced by the low density/low oxygen culture methods described below are used in the biochemical manipulation and biochemical manipulation/CLQ methods to induce production of gangliosides, e.g., GM1.

In additional embodiments of the invention, immortalized cells, for example, CHO cells and human embryonic kidney cells, e.g., CHO-K1 cells and HEK293 cells, are used in the biochemical manipulation and biochemical manipulation/CLQ methods of this invention. In further embodiments, neuroblastoma cells isolated from animal sources including but not limited to the above-recited animal sources, including humans, and neuroblastoma cell lines (including but not limited to SHSY-5Y, SHSY-S, and SK-N-AS) are used in the biochemical manipulation and biochemical manipulation/CLQ methods of the invention. In further embodiments, the cells for use in the biochemical manipulation and biochemical manipulation/CLQ methods of the present invention are derived from animals afflicted with gangliosidosis, e.g., humans, cats or dogs afflicted with GM1 gangliosidosis, GM2 gangliosidosis, or both. In further embodiments, bone marrow cells and fibroblasts from human, sheep, cats or dogs afflicted with gangliosidosis are used in the biochemical manipulation and biochemical manipulation/CLQ methods of the present invention. In embodiments, the fibroblast is a GM1 fibroblast.

In embodiments, each cell type used in the biochemical manipulation and biochemical manipulation/CLQ methods of the invention is cultured under the low density/low $O_2$ culture methods described in detail below prior to and/or during and/or after biochemical manipulation.

In embodiments, PC12 cells, HT22 cells, brain cells from a sheep afflicted with gangliosidosis, and fibroblast cells from a sheep afflicted with gangliosidosis are not used in the biochemical manipulation and biochemical manipulation/CLQ methods of the invention.

In embodiments, cells derived from the desired source are cultured in standard growth medium, e.g., Alpha-MEM supplemented with serum, e.g., 10% FBS, additionally supplemented with 1 to 4 mM glutamine under standard seeding density, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, e.g., 2,000 to 20,000 cells/cm$^2$, and preferably 8,000 cells/cm$^2$, at 37° C. in a humidified incubator under standard (5% $CO_2$) atmospheric conditions. In an additional embodiment, the amount of gangliosides, e.g., GM1, in the cell culture is quantified using the methods of the present invention. The gangliosides, e.g., GM1, can also be isolated and purified from the cell culture using standard methods, such as those described below.

In additional embodiments of the invention, the biochemical manipulation and biochemical manipulation/CLQ methods increases the accumulation of all gangliosides. In one embodiment of the invention, the biochemical manipulation and biochemical manipulation/CLQ methods increases the accumulation of GM1. In another embodiment of the invention, the biochemical manipulation and biochemical manipulation/CLQ methods increases the accumulation of GM2. In another embodiment of the invention, the biochemical manipulation and biochemical manipulation/CLQ methods increases the accumulation of GM3. In another embodiment of the invention, the biochemical manipulation and biochemical manipulation/CLQ methods increases the accumulation of GD1a. In another embodiment of the invention, the biochemical manipulation and biochemical manipulation/CLQ methods increases the accumulation of GD1b. In another embodiment of the invention, the biochemical manipulation and biochemical manipulation/CLQ methods increases the accumulation of GD3. In another embodiment of the invention, the biochemical manipulation and biochemical manipulation/CLQ methods increases the accumulation of GT1.

In another embodiment, the biochemical manipulation and biochemical manipulation/CLQ methods increase the accumulation of two or more gangliosides. In a further embodiment, the biochemical manipulation and biochemical manipulation/CLQ methods increase the accumulation of three or more gangliosides. In a further embodiment, the biochemical manipulation and biochemical manipulation/CLQ methods increase the accumulation of four or more gangliosides. In a further embodiment, the biochemical manipulation and biochemical manipulation/CLQ methods increase the accumulation of five or more gangliosides.

In additional embodiments of the invention, the biochemical manipulation and biochemical manipulation/CLQ methods results in 10 to 200 percent or about 10 to 200 percent more ganglioside accumulation in a cell compared with a cell that has not been biochemically manipulated and biochemically manipulated/CLQ treated. In another embodiment of the invention, the biochemical manipulation and biochemical manipulation/CLQ methods results in 15 to 125 percent or about 15 to 125 percent more ganglioside accumulation than a cell that has not been biochemically manipulated and biochemically manipulated/CLQ treated. In another embodiment of the invention, the biochemical manipulation and biochemical manipulation/CLQ methods results in 30 to 100 percent or about 30 to 100 percent more ganglioside accumulation than a cell that has not been biochemically manipulated and biochemically manipulated/CLQ treated. In another embodiment of the invention, the biochemical manipulation and biochemical manipulation/CLQ methods results in 60 to 80 percent or about 60 to 80 percent more ganglioside accumulation than a cell that has not been biochemically manipulated and biochemically manipulated/CLQ treated. In another embodiment of the invention, the biochemical manipulation and biochemical manipulation/CLQ methods results in 15, 19, 28, 63, 65, 83, 104, and 119 percent or about 15, 19, 28, 63, 65, 83, 104, and 119 percent more ganglioside accumulation than a cell that has not been biochemically manipulated and biochemically manipulated/CLQ treated. In another embodiment of the invention, the biochemical manipulation and biochemical manipulation/CLQ methods results in 65 percent more ganglioside accumulation than a cell that has not been biochemically manipulated and biochemically manipulated/CLQ treated.

The invention further provides a ganglioside produced by the biochemical manipulation and biochemical manipulation/CLQ methods of the invention.

The invention further provides methods of treating a subject having a disease or disorder in need of such treatment by administering a ganglioside, e.g., GM1, produced by the biochemical manipulation and biochemical manipulation/CLQ methods of the invention. In embodiments, a subject having neuronal injury is treated by administering a ganglioside, e.g., GM1, produced by the g biochemical manipulation and biochemical manipulation/CLQ methods of the invention. In embodiments, a subject having Parkinson's disease is treated by administering a ganglioside, e.g., GM1, produced by the biochemical manipulation and biochemical manipulation/CLQ methods of the invention. In embodiments, a subject having Alzheimer's disease is treated by administering a ganglioside, e.g., GM1, produced by the biochemical manipulation and biochemical manipulation/CLQ methods of the invention. In embodiments, a subject who has had or is having a stroke is treated by administering a ganglioside, e.g., GM1, produced by the biochemical manipulation and biochemical manipulation/CLQ methods of the invention. In embodiments, a subject having Guillain-Barré syndrome is treated by administering a ganglioside, e.g., GM1, produced by the biochemical manipulation and biochemical manipulation/CLQ methods of the invention. In embodiments, a subject having cancer is treated by administering a ganglioside, e.g., GM1, produced by the biochemical manipulation and biochemical manipulation/CLQ methods of the invention.

Long Term Cell Culture without Chemical Treatment and without Passaging

The invention further provides methods of producing gangliosides, e.g., GM1, by culturing cells without passaging and without neuronal induction media, chloroquine, or neuraminidase treatment. It has been surprisingly found that, cells cultured at high density, for example, at 60-90% confluence at time of seeding, or preferably 70-80% confluence at time of seeding, for long term remain viable and accumulate gangliosides, e.g., GM1, in significant quantities. In additional embodiments, the high density, long term culture methods of the invention are combined with the chemical treatments and/or biochemical disclosed above. For example, cells cultured with NIM/CLQ are then subjected to high density-long term culturing without passaging, or cells treated with CLQ and/or neuraminidase and/or glucosamine are cultured at high density for long term without passaging or cells are cultured at high density for long term without passaging and then treated with NIM/CLQ, CLQ, neuraminidase, and/or glucosamine.

Sources for cells for use in the high density, long term culturing methods of the invention include, but are not limited to, human, sheep, rabbit, mouse, guinea pig, horse, pig, cat and dog. In embodiments of the invention, fibroblasts and stromal cells, e.g., bone marrow and adipose-derived cells; and fibroblasts, e.g., GM1 fibroblast and dermal fibroblasts, from animal sources, including but not limited to the above recited animal sources can be used in the high density, long term culturing methods of the invention. Exemplary methods for isolating cells from animal sources are described in detail below. In embodiments, human bone marrow cells produced by the low density/low oxygen culture methods described below are used in the high density, long term culturing methods of the invention to induce production of gangliosides, e.g., GM1.

In further embodiments, neuroblastoma cells isolated from animal sources including but not limited to the above-recited animal sources, including humans, and neuroblastoma cell lines (including but not limited to SHSY-5Y, SHSY-S, and SK-N-AS) are used in the high density, long term culture methods of the invention.

In additional embodiments of the invention, immortalized cells, for example, CHO cells and human embryonic kidney cells, e.g., CHO-K1 cells and HEK293 cells, are used in the biochemical manipulation and biochemical manipulation/CLQ methods of this invention. In further embodiments, neuroblastoma cells isolated from animal sources including but not limited to the above-recited animal sources, including humans, and neuroblastoma cell lines (including but not limited to SHSY-5Y, SHSY-S, and SK-N-AS) are used in the high density, long term culture methods of the invention. In further embodiments, the cells for use in the high density, long term culture methods of the invention are derived from animals afflicted with gangliosidosis, e.g., humans, cats or dogs afflicted with GM1 gangliosidosis, GM2 gangliosidosis, or both. In further embodiments, bone marrow cells and fibroblasts from human, sheep, cats or dogs afflicted with gangliosidosis are used in the high density, long term culture methods of the invention. In embodiments, the fibroblast is a GM1 fibroblast.

In embodiments, each cell type used in the high density, long term culture methods of the invention is cultured under the low density/low $O_2$ culture methods described in detail below prior to and/or during and/or after culturing in the high density, long term culture methods of the invention.

In embodiments, PC12 cells, HT22 cells, brain cells from a sheep afflicted with gangliosidosis, and fibroblast cells from a sheep afflicted with gangliosidosis are not used in the high density, long term culture methods of the invention.

In such methods, the cells are maintained to accumulate gangliosides, e.g., GM1, and the culture medium is replaced, or additional culture media is added, as necessary to maintain cell viability. In embodiments, the cells are cultured in standard growth medium, such as Alpha-MEM supplemented with 10% FBS, MEM/F-12 supplemented with 10% FBS; EMEM/F-12 supplemented with 1% nonessential amino acids ("NEAA"), 2 mM L-glutamine and 15% FBS; DMEM supplemented with 0.1 mM NEAA and 10% FBS; F-12K supplemented with 10% FBS; EMEM supplemented with 10% FBS; Lonza MSC basal medial supplemented with growth supplements; Lonza ADSC basal medium supplemented with growth supplements; Lonza fibroblast basal medium with supplements; or EMEM supplemented with 15% FBS, for 4 days to 4 weeks, 6 days to 2 weeks, or 9 days to 12 days at approximately 37° C. in a humidified incubator under 5% $CO_2$ atmosphere. In an exemplary embodiment, the media is changed every 3 days to maintain cell viability.

Preferred cells for use in this embodiment of the invention include bone marrow- and brain-derived cells. Preferred brain- and bone marrow-derived cells include cells isolated from sheep and human using the low density/low oxygen conditions disclosed below. Preferably, the cells are derived from sheep or humans afflicted with gangliosidosis. Additional cell types for use in this embodiment of the invention include immortalized cells, stromal cells, and fibroblasts. Further cells types include neuroblastoma cells, e.g., primary cells or cell lines, including but not limited to SHSY-5Y, SHSY-S, and SK-N-AS. In embodiments, following high density, long-term culturing, the cells are harvested and gangliosides, e.g., GM1, are isolated and purified from the cells. In embodiments, the amount of gangliosides, e.g., GM1, in the cells is quantified using the methods of the invention.

In additional embodiments of the invention, the high density, long term culture methods increases the accumulation of all gangliosides. In one embodiment of the invention, the high density, long term culture methods of the invention increases the accumulation of GM1. In another embodiment of the invention, the high density, long term culture methods of the invention increases the accumulation of GM2. In another embodiment of the invention, the high density, long term culture methods of the invention increases the accumulation of GM3. In another embodiment of the invention, the high density, long term culture methods of the invention increases the accumulation of GD1a. In another embodiment of the invention, the high density, long term culture methods of the invention increases the accumulation of GD1b. In another embodiment of the invention, the high density, long term culture methods of the invention increases the accumulation of GD3. In another embodiment of the invention, the high density, long term culture methods of the invention increases the accumulation of GT1.

In another embodiment, the high density, long term culture methods of the invention increases the accumulation of two or more gangliosides. In a further embodiment, the high density, long term culture methods of the invention increases the accumulation of three or more gangliosides. In a further embodiment, the high density, long term culture methods of the invention increases the accumulation of four or more gangliosides. In a further embodiment, the high density, long term culture methods of the invention increases the accumulation of five or more gangliosides.

In additional embodiments of the invention, high density, long term culture methods results in 10 to 200 percent or about 10 to 200 percent more ganglioside accumulation in a cell compared with a cell that has not been cultured under high density, long term culture conditions. In another embodiment of the invention, high density, long term culture methods results in 15 to 125 percent or about 15 to 125 percent more ganglioside accumulation than a cell that has not been cultured under high density, long term culture conditions. In another embodiment of the invention, high density, long term culture methods results in 30 to 100 percent or about 30 to 100 percent more ganglioside accumulation than a cell that has not been cultured under high density, long term culture conditions. In another embodiment of the invention, high density, long term culture methods results in 60 to 80 percent or about 60 to 80 percent more ganglioside accumulation than a cell that has not been cultured under high density, long term culture conditions. In another embodiment of the invention, high density, long term culture methods results in 15, 19, 28, 63, 65, 83, 104, and 119 percent or about 15, 19, 28, 63, 65, 83, 104, and 119 percent more ganglioside accumulation than a cell that has not cultured under high density, long term culture conditions. In another embodiment of the invention, high density, long term culture methods results in 65 percent more ganglioside accumulation than a cell that has not been cultured under high density, long term culture conditions.

The invention further provides a ganglioside produced by the long term culture methods of the invention.

The invention further provides methods of treating a subject having a disease or disorder in need of such treatment by administering a ganglioside, e.g., GM1, produced by the long term culture methods of the invention. In embodiments, a subject having neuronal injury is treated by administering a ganglioside, e.g., GM1, produced by the long term culture methods of the invention. In embodiments, a subject having Parkinson's disease is treated by administering a ganglioside, e.g., GM1, produced by the long term culture methods of the invention. In embodiments, a subject having Alzheimer's disease is treated by administering a ganglioside, e.g., GM1, produced by the long term culture methods of the invention. In embodiments, a subject who has had or is having a stroke is treated by administering a ganglioside, e.g., GM1, produced by the long term culture methods of the invention. In embodiments, a subject having Guillain-Barré syndrome is treated by administering a ganglioside, e.g., GM1, produced by the long term culture methods of the invention. In embodiments, a subject having cancer is treated by administering a ganglioside, e.g., GM1, produced by the long term culture methods of the invention.

Gangliosides Produced by the Methods of Invention and their Methods of Use

The invention provides gangliosides produced by the methods of the invention.

Such gangliosides includes but are not limited to GM1, GM2, GM3, GD1a, GD1b, GD3, and GT1. The gangliosides produced by the invention differ from gangliosides produced by prior methods.

Gangliosides exist as a very complex mixture of species differing in both the hydrophilic and hydrophobic moieties. Sonnino and Chigorno, *Biochim Biophys Acta* 1469:63-77 (2000), incorporated by reference in its entirety. Gangliosides consist of a lipid moiety linked to a very large family of oligosaccharide structures differing in glycosidic linkage position, sugar confirmation, neutral sugar and sialic acid content. For example, commercially available GM1 gangliosides exhibit variations in long chain base. See Example 13 and Table 5. Accordingly, variations in structure exist even among gangliosides characterized as the same ganglioside, e.g., "GM1." Further, ganglioside composition differ between species and changes with age. Ikeda, et al., *J. Lipid Res.* 49:2678-2689 (2008); Masserini and Freire, *Biochem.* 25:1043-1049 (1986); Taketomi et al., *Acta Biochim. Pol.* 45:987-999, each of which is incorporated by reference in its entirety. For example, native GM1 is a heterogeneous mixture containing primarily C18:1 and C20:1 long chain bases. Id. In humans, GM1 composition changes over time. Taketomi et al., *Acta Biochim. Pol.* 45:987-999, incorporated by reference in its entirety. More specifically, the proportion of d20:1 (icosasphingosine) and d20 (icosa-sphinganine) of the total sphingosine bases increases quickly until adolescent or adult age and then remains constant at about 50%; this value was higher than the proportion of d20:1 and d20 of GM1 in various adult mammalian brains. Id.

In embodiments, the invention provides a ganglioside produced by the methods of the invention.

In further embodiments, the invention provides methods of treating a subject in need of treatment having a disease or disorder by administering a ganglioside produced by the methods of the present invention. Exemplary disease or disorders include, but are not limited to neuronal injury, Parkinson's disease, Alzheimer's disease, stroke, Guillain-Barré syndrome, and cancer.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The terms "treat" or "treatment" when used in the context of the use of gangliosides produced by the invention, includes but is not limited to therapeutic treatment and prophylactic or preventative measures, wherein the object is to prevent or slow down (lessen) an undesired physiological change or disorder, such as the development of Parkinson's disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" in this context can also mean prolonging survival as compared to expected survival if not receiving treatment. Those in need of treatment include those already with the condition or disorder as well as those prone to have the condition or disorder or those in which the manifestation of the condition or disorder is to be prevented.

Additionally, the term "treatment" when used in the context of cell culture, includes but is not limited administration or application of cultured cells to a specified drug, chemical, technique, therapy and/or method.

By "subject" or "individual" or "animal" or "patient" or "mammal," is meant any subject, particularly a mammalian subject, e.g., a human patient, for whom diagnosis, prognosis, prevention, or therapy is desired.

Methods of Producing the Cells for Use in the Methods of the Invention

As noted above, in embodiments, cells are utilized in the methods of the invention. In such embodiments, the cells can be obtained by culturing under low oxygen, low density conditions. Such methods are known in the art, and are disclosed in, for example, U.S. Publication Nos. 2003/0059414, 2007/0224177 and 2009/0053183 (patented as U.S. Pat. No. 8,354, 370 B2), each of which is herein incorporated by reference in its entirety. In one embodiment bone marrow-derived cells are utilized in the methods of the invention. In such embodiment, bone marrow-derived cells can be obtained by culturing under low oxygen, low density conditions.

In an exemplary embodiment, whole bone marrow aspirates are obtained from sheep or a human and cultured in contact with a solid phase. For example, human bone marrow cells are obtained from healthy human donors by aspirations of the iliac crest and bone marrow stromal cell populations obtained employing well-established techniques. If desired, the whole bone marrow aspirate can be processed to yield a mononuclear cell fraction that is then cultured in contact with a solid phase. The solid phase can be, for example, plastic (e.g., tissue culture treated plastics)

The mononuclear cell fraction can be obtained from a whole bone marrow aspirate on a density gradient by established procedures. Alternatively, the mononuclear cell fraction is obtained by lysis of the red blood cells contained in the bone marrow aspirate. Lysis is accomplished by mixing the bone marrow aspirate with ammonium chloride.

The bone marrow aspirate, or a cellular fraction of the bone marrow aspirate, is cultured in contact with a solid phase and an intermediate cell population is isolated from the resulting cell culture based on their propensity to adhere to the solid phase. Bone marrow aspirates, or a cellular fraction of the aspirate, are cultured at a dissolved oxygen concentration of less than about 20%, preferably between about 1% to about 10%, and most preferably from between about 2% oxygen to about 7% oxygen. In a preferred embodiment, the dissolved oxygen concentration is about 5% oxygen. The resulting adherent cell population is expanded to yield a substantially homogeneous cell population which co-express CD49c and CD90.

Bone marrow cell expansion is conducted with a seeding density of less than about 2500 cell/cm$^2$, preferably less than about 1000 cells/cm$^2$, and most preferably less than about 100 cells/cm$^2$. In a particular embodiment, the initial cell density in the expansion step is between about 30 cells/cm$^2$ to about 50 cells/cm$^2$. A seeding density would be the number of adherent cells per cm$^2$ obtained from mononuclear bone marrow cells.

Standard media preparations can be used to culture the bone marrow cells. For example, the media can be Alpha-MEM modification supplemented with 4 mM L-glutamine and 0 to 10% lot selected FBS, preferably about 10% FBS. The culturing step can be conducted for any reasonable period, e.g., between about 3 to about 25 days and most preferably between about 3 to about 15 days.

An intermediate cell population is isolated from the cell culture describe above based on its propensity to adhere to the solid phase. The intermediate cell population is grown at a cell concentration that encourages virtually only the self-renewing cells, referred to herein as colony-forming unit fibroblast-like cells (CFU-F), to proliferate. The CFU-F-derived cells are sub-cultured under defined conditions to produce a substantially homogeneous population of cells. According to the invention, the expansion yields a substantially homogeneous cell population which co-express CD 49 and CD 90.

Methods of Isolating Sheep Brain-Derived Cells for Use in the Methods of the Invention As discussed above, in embodiments, sheep brain-derived cells are utilized in the methods of the invention. For example, in some embodiments, sheep brain-derived cells are cultured using the long-term, high density culturing methods of the present invention. As noted above, in some embodiments, sheep brain-derived cells are isolated from sheep afflicted with gangliosidosis. Sheep afflicted with gangliosidosis have been disclosed previously, for example, in U.S. Pat. No. 5,532,141, which is incorporated herein by reference in its entirety. Isolation and culture methods of sheep brain-derived cells are disclosed in the art, for example, in Int'l. Appl. No. PCT/US2010/047522, published as WO 2011/028795, which is herein incorporated by reference in its entirety.

In an exemplary embodiment, cells are isolated from the following sheep brain tissue sources: centrum semiovale, cerebellar cortex, hippocampus, caudate nucleus, cerebral cortex (e.g., frontal, parietal), and ventricular walls. Each tissue type is rinsed with PIPES buffer, and digested in papain/DNase I/Dispase (neutral protease) with antibiotics/antimycotics. The enzymes are neutralized and dissociated cells are passed through a cell strainer. Cells are centrifuged and re-suspended in DMEM/F12/N2 supplemented with 5% FBS and antibiotics/antimycotics. Cells are enumerated and seeded in fibronectin-coated flasks in DMEM/F12/N2 supplemented with 5% FBS and antibiotics/antimycotics and additionally supplemented with 10 ng/ml bFGF and 20 ng/ml EGF or Neurocult Proliferation-A medium. Cells in each media type are grown in a 37° C. humidified incubator. In embodiments, the cells are grown in low oxygen conditions, e.g., 20% or less, 15% or less, 10% or less, and preferably 4% or 5% oxygen, before utilizing the methods of the invention.

Methods of Isolating Gangliosides from Cells

Extraction and purification of gangliosides from the cell cultures of the present invention is accomplished by methods known in the art. For example, sonicate cell pellet in minimal amount of water for 30 minutes to homogenize. Dilute sample to 20 volumes in 2:1 Chloroform:Methanol. Sonicate for 30 minutes. Centrifuge at 2000 rpm for 15 minutes to pellet cell material. Decant and save supernatant. Suspend pellet in 10 volumes of 2:1 Chloroform:Methanol containing 5% water. Sonicate for 30 minutes. Centrifuge and decant as before. Combine supernatants. Repeated addition of chloroform:methanol, sonication and centrifugation 2-3 additional time to fully extract all gangliosides. The vast majority of the gangliosides should be extracted in the first two extraction cycles. To the combined supernatants add 0.2 volumes of 0.1N KCl or NaCl. Mix well. Centrifuge at 2000 rpm for 15 minutes to separate layers. Save upper layer. To the remaining organic (lower) layer, add 0.2 volumes of 1:1 Methanol: 0.1N KCl or NaCl. Mix well. Repeat the steps of addition of KCl or NaCl, centrifugation, and extraction. To the remaining organic (lower) layer, add 0.2 volumes of 1:1 Methanol:Water. Combine the saved upper layers and concentrate. The resulting extract contains a pool of gangliosides. The species of interest can then be further isolated using column chromatograph, e.g., sepharose or cholera-toxin B.

Quantifying the Amount of Gangliosides in Cell Culture

The invention also provides methods of quantifying the amount of gangliosides, e.g., GM1, in the cell culture after practicing the ganglioside production methods of the present invention. Accordingly, the invention provides methods for producing a standard curve for plate-based ganglioside, e.g., GM1, quantification for which to compare samples against.

In some embodiments, a standard curve is generated by preparing dilutions of gangliosides, e.g., GM1, such as sheep or human GM1 and adding the dilutions to an ELISA plate, such as a Nunc MaxiSorp® plate. The plates are incubated to allow adsorption of the gangliosides, e.g., GM1, to the plates, for example, for 8 to 24 hours, and preferably 12 to 16 hours at 4° C. After incubation, the plates are washed and blocked, and the gangliosides, e.g., GM1, is contacted with CTB, which is conjugated to a dye or to an enzyme that generates a colored end-product upon contacting its substrate. After contact with the CTB conjugate, the light emitted by or absorbed by the dye or the colored end-product, is measured, wherein the readings indicate the amount of gangliosides, e.g., GM1, in the purified ganglioside, e.g., GM1, coating the plate. In an embodiment, the absorbance is read on a standard plate reader. A standard curve is generated from the absorbance data, for which to compare the test data against.

The standard curve is subsequently used to compare readings of test wells to quantify the amount of gangliosides, e.g., GM1, accumulated in the cells or, in embodiments, the amount of gangliosides, e.g., GM1, after solubilization. In an exemplary embodiment, the test wells contain adherent ganglioside-containing cells, which are washed and blocked in the same manner as the sample plate, above. The adherent cells are contacted with CTB, which is conjugated to a dye or an enzyme that generates a colored end-product upon contact with its substrate. The light emitted by or absorbed by the dye or the colored end-product is measured and compared with the standard curve to determine the amount of gangliosides accumulation in the adherent cells. After this reading is completed, the gangliosides can be solubilized using, for example, 1% SDS in PBS, and the plates re-read on the plate reader. Gangliosides can be bound to other molecules in the cells, rendering the CTB binding site inaccessible to the detection agents, CTB-HRP or CTB-Alexa488, for example. The solubilization releases the bound or aggregated ganglioside to provide an additional quantification value.

In embodiments, preferred dyes are fluorescent dyes, such as green fluorescent dyes. In embodiments, the dye is FITC or Alexa488. In additional embodiments, the enzyme that is conjugated to CTB is horseradish peroxidase ("HRP"). In the case of a CTB-HRP conjugate, ABTS reagent is contacted with the adherent cells to create a colored product and absorbance of the colored product is measured.

EXAMPLES

Example 1

A T-225 Tissue culture flask (Corning, Cat #431081) was seeded with the sheep bone marrow-derived cells (Passage 1 or 2) in Alpha-MEM growth medium (with 10% FBS) at a density of 8,000 cells/cm$^2$.

The next morning, medium was replaced with 30 ml Neuronal induction medium (NIM): Neurobasal Medium+B27 supplement with Retinoic acid, EGF (25 ug/ml) and FGF (10 ng/ml).

In the evening, 50 μM chloroquine was added to the flask. About 70% cell death was observed on the $3^{rd}$ day. The floating cells were removed from the flask by rinsing with PBS. The cells were trypsinized and surviving cells were collected. The cells were spun down and re-suspended in fresh growth medium. New flask was seeded at 8,000 cells/$cm^2$. An aliquot was removed and plated in a 24-well plate for confirming GM1 induction by staining with Cholera toxin conjugated to Alexa488. Compared to untreated (Control) cells, SBM treated with NIM/CLQ (48 h CQ in NIM) have much strong staining for GM1, as shown in FIGS. 1A and 1B.

The surviving cells were allowed to expand in the flask for 2 days, and the cells were then harvested.

Alternatively, the surviving cells can be treated for a second time with 50 uM CLQ for 24 h before harvesting.

Example 2

Adult Human Bone Marrow Cells were seeded in standard tissue culture flasks at a seeding density of 8000 cells/$cm^2$ in Alpha-MEM growth medium (with 10% FBS).

Next day the medium was replaced, if required, and 50 uM CLQ was added to the flask. The cells were harvested after 48 h. About 10-20% cell death was observed. Fixed cells were stained with CTB-Alexa488 to visualize GM1 levels. Compared to the upper panel (control), the CLQ-treated cells (lower panel) showed significantly higher accumulation of GM1.

Example 3

The objective of this example was to up-regulate GM1 expression in human neuroblastoma cell line, SHSY-5Y, sheep bone marrow-derived cells (SBM) and human bone marrow-derived cells (HBM)

In one study SHSY-5Y cells, SBM and HBM were seeded in growth media with 10% serum in 24-well plates. The next day, the cells were subjected to 3 different treatment regimens or left in growth media (AMEM with 10% FBS):

Serum-free medium (SFM)
Neuronal induction medium (NIM)
50 uM Chloroquine (CLQ)

After 48 hours, 100 ul of Alamar Blue dye was added to the wells and incubated for 1 hour. The absorbance of Alamar Blue was measured using a plate reader. The plates were then washed, fixed and processed for GM1 staining using CTB-HRP. Values of CTB-HRP were normalized to Alamar Blue values, which are indicative of surviving cells.

As shown in FIG. 3, all 3 cell types showed some up-regulation of GM expression in the NIM (compare control to NIM). SHSY-5Y cells showed about a 2-fold induction in NIM, whereas SBMCs showed about 4-fold induction. The most dramatic up-regulation of GM1 expression, approximately 8-fold, was seen with CLQ treatment of HBMCs (compare control to ClQ for HBM) (see FIG. 3).

In a series of studies SHSY-5Y, sheep bone marrow-derived and human bone marrow-derived cells were treated with compounds that are known to affect ganglioside pathways. Chloroquine is an acidotropic agent that perturbs membrane trafficking from endosomes to lysosomes. A23187 is a calcium ionophore that promotes exosome secretion after CLQ treatment. N-acetylglucosamine activates the hexosamine pathway, which provides intermediates for the synthesis of glycoconjugates. Switching to galactose as a carbohydrate source can modify the composition of gangliosides. Since neurons express higher levels of GM1 compared to other cell types, the cells were pushed towards a neuronal phenotype by treating with compounds and media known to induce neuronal differentiation (NIM).

SHSY-5Y cells were seeded at 10,000 cells/well in 24 well plates and treated according to the conditions listed in Table 1 below. After treatment the cells were fixed and stained with CTB-Alexa 488 to detect GM1. The intensity of the staining, amount of cell death and other observations were noted and summarized. The results are presented in Table 1. Treatment of SHSY-5Y with NIM2 media produced the most intense staining (five plus signs) and no cell death (one minus sign). Glucosamine and CLQ plus A23187, a calcium ionophore, treatments also resulted in strong induction of GM1 (four pluses) with some cell death in the CLQ plus A23187 group. CLQ alone showed more staining that control treated cells.

TABLE 1

Induction of GM1 in SHSY-5Y cells by different treatment conditions.

| Treatment | Time | Staining Intensity | Cell Death | Observations |
| --- | --- | --- | --- | --- |
| Control | | ++ | − | Bright staining in membrane. Mostly uniform |
| Glucosamine (0.5 mM) | 48 H | ++++ | − | Brighter, uniform staining. A more differentiated morphology with short branched neuritis |
| Chloroquine (50 uM) | 24 H | +++ | + | Vesicular accumulation of staining seen inside the cells |
| Chloroquine + A23187 (1 mM) | 24 H + 30 MIN | ++++ | + | Vesicular accumulation + a few bright patches in membranes |
| NIM (Neurobasal + B27 + FGF, EGF + RA) | 48 H | +++++ | − | Bright staining all over, differentiated morphology with short unbranched neuritis |

TABLE 1-continued

Induction of GM1 in SHSY-5Y cells by different treatment conditions.

| Treatment | Time | Staining Intensity | Cell Death | Observations |
|---|---|---|---|---|
| Switch from No glucose to galactose | 24 H -> 48 H | ++ | – | More neuritis, but no increase in staining intensity |

Affected sheep bone marrow cells (SBM) were seeded at 20,000 cells/well in 24 well plates and treated according to the conditions listed in Table 2 below. After treatment the cells were fixed and stained with CTB-Alexa 488 to detect GM1. The intensity of the staining, amount of cell death and other observations were noted and summarized. The results are presented in Table 2. Treatment of SBM cells with CLQ in NIM media produced the most intense staining (four plus signs) and the most cell death (three plus signs). CLQ alone also induced GM1, but not as much as CLQ/NIM. Other conditions, serum-free media, NIM(1) media, glucosamine and PDGF also induced GM1, but to a lesser degree.

TABLE 2

GM1 Induction in Affected Sheep Bone Marrow cells by different treatments.

| Treatment | Treatment Time | Degree of GM1 Staining | Degree of Cell Death | Observations |
|---|---|---|---|---|
| CONTROL | | + | – | Mixed population. A few cells are bright all over. Most stain faintly |
| SERUM-FREE MEDIUM | 72 H | ++ | – | More number of brighter cells |
| NIM(1) (Neurobasal + B27 + EGF, FGF) | 72 H | ++ | – | Some change in morphology. Some bright cells. No significant difference overall in staining compared to control |
| NIM | 72 H | ++ | – | More spindle-like cells, The thin, elongated cells are brighter. But overall no significant increase in staining. |
| CHLOROQUINE | 72 H | +++ | + | Vesicular accumulation seen in most cells. Few cells are very bright. |
| CHLOROQUINE IN NIM | 72 H | ++++ | +++ | Most cells died, but the ones that survived are very bright all over. |
| GLUCOSAMINE | 72 H | ++ | – | A uniform increase in peri-nuclear staining. More prominent adhesion sites |
| PDGF | 72 H | ++ | – | Increase in perinuclear staining, and some bright patches in the membrane. |
| Poly-L-Lysine coated coverslips | 6 Days | + | – | Slightly brighter than cells grown on 24-well plate. Transient changes in morphology (neuronal phenotype) seen in NIM |

Human bone marrow cells (HBM) were seeded at 20,000 cells/well in 24 well plates and treated according to the conditions listed in Table 3 below. After treatment the cells were fixed and stained with CTB-Alexa 488 to detect GM1. The intensity of the staining, amount of cell death and other observations were noted and summarized. The results are presented in Table 3. Treatment of HBM cells with CLQ produced the most intense staining (five plus signs) and some cell death (two plus signs). Unlike SBM, NIM-CLQ treatment resulted in death of majority of the cells. Serum-free media also induced GM1, but not as much as CLQ.

TABLE 3

GM1 Induction in Human bone marrow-derived cells by different treatments.

| Treatment | Treatment Time | Degree of GM1 Staining | Degree of Cell Death | Observations |
| --- | --- | --- | --- | --- |
| CONTROL | | + | − | Mixed population. A few cells are bright all over. Most stain faintly. More brighter cells than SBM |
| SERUM-FREE MEDIUM | 72 H | ++ | − | More number of brighter cells |
| CHLOROQUINE | 48 H | +++++ | ++ | Huge accumulation seen in most cells. A lot of cells look bi-polar |
| CHLOROQUINE IN NIM | 48 H | | ++++ | Most cells died |

Example 4

Mouse Neuro2A neuroblastoma cells were cultured in standard growth media (DMEM F12 high glucose, 2 mM glutamine, 25 mM HEPES plus 10% FBS). Cells were maintained in standard culture media (Ctrl) or treated for 3 hours with neuraminidase, 1 unit/ml (Treated). Cells were fixed with 2% paraformaldehyde and stained with CTB-Alexa488 to detect GM1 ganglioside. Brightfield images of cell cultures prior to fixation are shown in panels A and C of FIG. 4. Fluorescent images showing GM1 positive staining are shown in panels B and D of FIG. 4. GM1 staining is dramatically stronger in mouse Neuro 2A cells after treatment with neuraminidase (compare panel B to D).

Example 5 hABM-SC were cultured in standard growth media (AMEM, 10% FBS, 2 mM glutamine). Cells were maintained in standard culture media (Control) or treated for 3 hours with neuraminidase, 1 unit/ml (Treated). Cells were fixed with 2% paraformaldehyde and stained with CTB-Alexa488 to detect GM1 ganglioside. Fluorescent images showing GM1 positive staining are shown in FIG. 5. GM1 is more abundant in hABM-SC after treatment with neuraminidase and often seen as large aggregates.

Example 6

Mouse Neuro2A neuroblastoma cells were plated at high density, greater than 40,000/cm$^2$, and cultured in standard growth media (DMEM F12 high glucose, 2 mM glutamine, 25 mM HEPES plus 10% FBS). Cells were maintained in standard culture media (Ctrl) for 3 or 9 days. Media was changed every 3 days. Cells were fixed with 2% paraformaldehyde and stained with CTB-Alexa488 to detect GM1 ganglioside. Brightfield images of cell cultures prior to fixation are shown in panels A and C. Fluorescent images showing GM1 positive staining are shown in panels B and D of FIG. 6. Extensive GM1 accumulation is evident in mouse Neuro2A cells maintained in culture at high density for long term compared to basal levels of GM1 in cells maintained in culture at lower density for 3 days or less (compare panel B to D of FIG. 6).

Example 7

Sheep brain-derived cells were cultured in standard growth media (AMEM, 10% FBS, 2 mM glutamine). Cells were maintained in standard culture media for 3 or 9 days. Media was changed every 3 days. Cells were fixed with 2% paraformaldehyde and stained with CTB-Alexa488 to detect GM1 ganglioside. Fluorescent images showing GM1 positive staining are shown in panels B and D of FIG. 7. Extensive GM1 accumulation is evident in sheep brain-derived cells maintained in culture at high density for long term compared to basal levels of GM1 in cells maintained in culture at lower density for 3 days or less (compare panel B to D in FIG. 7).

Example 8

Dilutions of purified ovine GM1 are prepared and added (100 μl of each dilution) to Nunc maxisorp plates. The plates are incubated overnight at 4° C. The following day plates are washed and blocked. CTB-HRP (75 ul per well, 1:4000) is added and the plates are incubated for 1 hr at RT in dark. Plates are washed and then ABTS reagent (100 μl per well) added. The green color is allowed to develop. The reaction is stopped with 66 ul of Stop solution (0.1% SDS in PBS). Signal is read on a standard plate reader. Data is plotted and standard curve is shown in FIG. 8. The sensitivity range is 3 ng-0 ng.

Example 9

Dilutions of purified ovine GM1 are prepared and added (100 μl of each dilution) to Nunc maxisorp plates. The plates are incubated overnight at 4° C. The following day plates are washed and blocked. CTB-Alexa488 (1:200) is added and the plates are incubated for 1 hr at RT in dark. Plates are washed and the signal is read on a standard plate reader. Next 1% SDS in PBS is added to solubilize the GM1 for 10-15 min. The plates are read again on the plate reader, the data is plotted and a standard curve is shown in FIG. 9. The sensitivity range is 500 ug-30 ug.

Example 10

A bone marrow aspirate from a single human donor was used to produce the Master Cell Bank, MCB105. The bone marrow harvest was performed by Cambrex (Gaithersburg, Md.) in accordance with Cambrex Bioscience Procedures. A total volume of 124 mL of bone marrow was obtained from bilateral aspirations from the posterior pelvic bone of the donor using standard medical procedures. The aspirate was placed in a sterile blood bag containing heparin and placed into a shipping container with a temperature recorder and a cold pack. Processing was initiated within 4 hours of bone marrow donation.

Bone Marrow Processing

All aseptic processing of the bone marrow aspirate occurred within a Class 100 biological safety cabinet. The aspirate was transferred from the blood bag to a sterile 250 mL container. The volume of the blood bag contents was measured and a sample of the aspirate was removed. Ten volumes of ACK-LYS solution (BioSource International: NH4Cl [8.29 g/L], KHCO3 [1.0 g/L], EDTA [0.037 g/L]) were added to the aspirate to lyse the red blood cells. The suspension was centrifuged to isolate the nucleated cells. The supernatant was discarded and the cells were resuspended with AFG104 growth media (alpha-MEM with 10% (v/v) Fetal Bovine Serum and 4 mM L-Glutamine) and washed two additional times with growth media by dilution and centrifugation. After the final wash step, the cells were resuspended in AFG104 growth media. A sample of the post lysing/washing suspension was removed and the nucleated cells enumerated and viability determined. The mononuclear cells were isolated from the bone marrow aspirate and used to seed five culture vessels, Nunc cell factories, with 60,000±2000 cells/cm2 (3.79×108 cells per factory). Each factory was supplemented with one liter of AFG104 growth medium. The cell factories were incubated in a 37° C. incubator and the cultures were aerated with 5% CO2 and 4% O2. The cultures were monitored twice daily for signs of contamination and to ensure the incubator culture conditions were within specifications (37°±2° C., 4.0%±0.5% O2, 5.0%±0.5% CO2). After seven days of growth, the media was removed from each factory and exchanged with fresh media.

The population doublings during the first expansion, resulting in MCB105, were determined to be 9.4 population doublings. MCB105 was filled as 2 mL aliquots into cryovials, cryogenically preserved and stored at ±−130° C. in the vapor phase of liquid nitrogen. Working Cell Bank 1 (WCB1) was produced from the expansion of MCB105. WCB1 is expanded for 7.5 to 9.5 population doublings, resulting in cumulative population doubling of 16.9 to 18.9. Harvested cells were aliquoted as 0.8 to 1 mL aliquots (10 to 20 million viable cells per vial) into cryovials cryogenically preserved and stored at ±−130° C. in the vapor phase of liquid nitrogen.

The expansion, cryofreezing and testing processes were repeated for WCB2 and WCB3. WCB2 and WCB3 were each expanded 7.5 to 9.5 population doublings. This expansion results in a cumulative population doubling of 24.4 to 28.4 for WCB2 and a cumulative population doubling of 31.9 to 37.9 for WCB3.

The Master Cell Banks, Working Cell Banks (WCB1, WCB2, WCB3), and GBT009 were aliquoted into cryovials, cryogenically preserved, and stored at −130° C. in the vapor phase of liquid nitrogen.

Cell Bank System

The cell bank system consists of five different banking procedures: MCB105, WCB1, WCB2, WCB3 and GBT009. MCB105 was 9.4 doublings. Each WCB was expanded for 7.5 to 9.5 population doublings resulting in three successive WCBs used to reach the target number of population doublings for (GBT009. Therefore MCB105 was expanded to 37.5 to 47.5 cumulative population doublings.

This cell bank system allows for the generation of new lots of WCB1, WCB2, WCB3 and GBT009 from MCB05 when a bank becomes depleted. For example, a depleted WCB2, lot#S1, can be regenerated as lot#S2 by expanding a vial from the same lot of WCB1, lot#F1-5, used to produce S1. The bank is thawed and follows the same expansion procedure and population doublings. This expansion process is the same for the establishment of all the working cell banks. The current WCB3 bank, lot#T2, after depletion will be reproduced as lot#T3 using the same WCB2 that was used to produce lot#T2. This methodology allows for the repeated production of WCB1, WCB2, WCB3 and vials of the final product, GBT009, lot numbers P5, P6, P7, etc. This approach allows for a high degree of reproducibility, consistency and quality in the manufacturing process and the cell product. All cell banks are stored in the vapor phase of liquid nitrogen (≤−130° C.).

After five days of additional incubation (12 days post seeding), the harvest of adherent colonies was accomplished by trypsinization. The conditioned media was removed from the cultures and tested by microbial fluid culture (no growth) and for mycoplasma (none detected). While the cells were attached to the cell factories, they were washed with 500 mL of dPBS (Dulbecco's Phosphate Buffered Saline without Calcium or Magnesium). The solution was removed and discarded as waste. Trypsin-EDTA was added to disassociate the cells from the factories. The cells were transferred to a sterile container and the trypsin-EDTA was neutralized by adding a volume of AFG104 growth media equal to the volume of trypsinized cells. The cell suspension was centrifuged and the cell pellets were resuspended in growth media.

Each resuspended cell suspension was sampled and tested for cell count, viability and purity. Upon acceptance of in-process test results, the cell suspensions were pooled. The pooled suspension was sampled and tested for cell number, viability, purity and identity. The suspension was then centrifuged and the supernatant was decanted and discarded. The cell pellet was resuspended in cryopreservation buffer, CSM-55 (Cryogenic Storage Media composed of Balanced Salt Solution, 4.5% w/v Dextrose, USP with 5% v/v Dimethyl Sulfoxide, USP and 5% v/v Human Serum Albumin, USP). The volume of CSM-55 was driven by the cell count of the suspension. CSM-55 was added to achieve a concentration of one million cells per mL. After the cells were resuspended in CSM-55, the suspension was sampled to confirm cell number, viability, purity and identity prior to cryopreservation.

Within the Class 100 biological safety cabinet, 259 vials of MCB105 were manually filled using aseptic techniques. Each 5 mL vial contained 2 mL of the CSM-55 cell suspension. During the filling operation, weight checks were performed on every 30th vial filled to track consistency in the vialing operation, and no discrepancies from the target volume (1.8 to 2.2 mL) were observed. Upon completion of the vialing operations, the vials were frozen using a controlled rate freezer. The cell suspension was cooled from ambient temperature to 4° C. Once the vials were equilibrated to 4° C., they were temperature stepped down to −120° C. and held at this temperature until removal for permanent storage. The vials of MCB105 are stored in the vapor phase of liquid nitrogen storage (−130° C.). Storage tanks have restricted access.

Preparation of Working Cell Banks (WCB1, WCB2, WCB3)

The manufacturing process involved the sequential production of three WCBs. Each successive cell bank was derived from an aliquot of cryogenically stored cells from the previous bank, i.e. MCB105→WCB1→WCB2→WCB3. All manipulations of the culture were performed in a Class 100 biological safety cabinet with an active environmental monitoring program. The production of each cell bank was initiated by thawing cells from the appropriate preceding cell bank. An aliquot of cells from MCB105 was removed from cryogenic storage, thawed and resuspended in AFG104 growth media creating a stock cell suspension. A sample from the stock solution was removed and tested for cell number and viability. The culture vessels, Nunc cell factories, used for each working cell bank were seeded at 30±5 cells per cm2 and cultured using AFG104 growth media. The cell factories were incubated in a 37° C. incubator and the cultures were aerated with 5% CO2 and 4% O2. After seven days of growth, the media were removed from each factory and exchanged with fresh media. The conditioned media was tested for microbial fluid culture. The factories were incubated for an additional period of time to achieve a population doubling of 7.5 to 9.5 doublings.

The isolation (harvest) of adherent colonies was accomplished by trypsinization. Conditioned media was removed from the culture and tested for sterility by microbial fluid culture and for mycoplasma. While the cells were attached to the culture vessel, the cells were washed with dPBS. The solution was removed and discarded as waste. The removal of cells was accomplished by adding trypsin-EDTA to the culture and allowing the cells to disassociate from the culture vessel. Cells were transferred to a sterile container and the trypsin-EDTA was neutralized by adding AFG104 growth media to the trypsinized cells. The cell suspension was centrifuged and resuspended in growth media. Samples of the resuspended cell suspension were taken from each cell factory and submitted for in-process testing (cell count, viability and purity). Cell suspensions from the individual factories met acceptance criteria prior to combining into a pooled cell suspension. When the cell suspensions were combined, the pooled suspension was sampled to confirm the cell number, viability, purity and identity. The suspension was then centrifuged. After centrifugation, the supernatant was decanted and the cell pellet was resuspended in cryopreservation buffer, CSM-SS, to achieve a concentration up to 20 million cells per mL. The suspension was sampled again to confirm the cell number, viability, purity and identity. The vials were aseptically and manually filled in a Class 100 biological safety cabinet in 1.0±0.2 mL aliquots into 2 mL polypropylene Corning cryovials. Weight checks were performed on every 25th vial to track consistency in the vialing operation. Upon completion of the vialing operations, the vials were frozen using a control rate freezer. The cell suspension was cooled from ambient to 4° C. and then temperature stepped down to ±−120° C. and held until removed for storage in the vapor phase of liquid nitrogen (±−130° C.).

Example 11

Human bone marrow-derived stromal cells, adipose-derived stromal cells, dermal fibroblasts, and fibroblasts from subjects diagnosed with GM1 gangliosidosis, as well as immortalized neuroblastoma cells (SHSY-5Y, SHSY-S and SK-N-AS), Chinese Hamster Ovary cells (CHO-K1), and Human Embryonic Kidney cells (HEK293) were purchased from commercial sources. Cells were cultured on 24 well plates in standard culture medium, at a density of 2000-20,000 cells/well overnight and either maintained in standard culture medium (CONTROL) or treated with chloroquine (CLQ) according to the conditions listed in Table 4 below. Cells were maintained in a tissue culture incubator at approximately 37° C. in a humidified atmosphere comprising approximately 5% $CO_2$ and approximately 21% $O_2$ balanced with $N_2$. After treatment for 48-120 hours, the cells were fixed with 4% paraformaldehyde and stained with CTB-Alexa488 to detect GM1 ganglioside. Fluorescent images showing GM1 positive staining are shown in FIGS. 10 and 11. Extensive GM1 accumulation is evident in most cells types compared to controls maintained in standard culture media alone. (FIGS. 10 and 11 and Table 4).

TABLE 4

GM1 induction in different cell-types by CLQ treatment.

| Cell Type | Media Formulation | Seeding Density (per well) | % Increase in Degree of Staining with induction |
|---|---|---|---|
| SHSY-5Y | MEM/F-12 + 10% FBS | 20,000 | 104 |
| SHSY-S | EMEM/F-12 + 1% NEAA + 2 mM L-glutamine + 15% FBS | 20,000 | 19 |
| SK-N-AS | DMEM + 0.1 mM NEAA + 10% FBS | 20,000 | 19 |
| CHO-K1 | F-12K + 10% FBS | 20,000 | 83 |
| HEK293 | EMEM + 10% FBS | 20,000 | 15 |
| GBT-ABMSC | Alpha-MEM + 10% FBS | 20,000 | 65 |
| Lonza BMSC | Lonza MSC basal medium + growth supplements | 10,000 | 119 |
| ADSC | Lonza ADSC basal medium + growth supplements | 10,000 | 28 |
| Dermal fibroblast | Lonza fibroblast basal medium + supplements | 7000 | 63 |
| GM1 fibroblast | EMEM + 15% FBS | 20,000 | 28 |

Example 12

One normal and one affected (Ovine GM1 gangliosidosis) sheep, approximately 4 months of age, were euthanized at the Holler Farm in South Dakota. A 5-10 ml scoop of bone marrow was collected from the femur of each animal and placed into separate labeled sterile 50-ml conical tubes. The tubes were filled with shipping solution (Hibernate A from Brain Bits, 1× Penicillin/Streptomycin from Invitrogen). Samples were shipped on ice to Malvern, Pa. in less than 24 hours. Upon receipt the outside of the tubes were cleaned and transferred to a sterile bio-safety cabinet. The shipping solution was decanted and 25 ml Dulbecco's Phosphate Buffered Solution (DPBS) was added to each bone marrow. Gently and repeatedly the bone marrow/DPBS solution were triturated to create a cell suspension. Each cell suspension was divided into 2 sterile 500 ml centrifuge tubes (Corning Life Sciences). To each centrifuge tube, 150 ml of ACK lysis solution (Invitrogen) was added. The solutions were mixed by pipetting the cell suspensions up and down 10-20 times. Each tube was capped and vortexed for 2 seconds. The cell suspensions were centrifuged for 10 minutes at 1350±50 RPM on low brake using an Allegra 6R centrifuge and swinging buckets. The supernatant from each sample was aspirated off and discarded. Each remaining cell pellet was resuspended in 10 ml of AFG104 growth media (AMEM, 10% fetal bovine serum, 4 mM glutamax, 1× penicillin/streptomycin, 1× Gentamycin). The 2 cell suspensions from normal sheep bone marrow were combined into a sterile 50 ml conical. The 2 cell suspensions from the affected sheep bone marrow were combined into a separate sterile 50 ml conical. AFG104 growth media was added to each cell suspension to a final volume of 40 ml. The samples were centrifuged for 10 minutes at 1350±50 RPM on low brake using an Allegra 6R centrifuge and swinging buckets. The supernatants were discarded. The cell pellets were separately re-suspended in 20 ml AFG104 growth media. The volume was adjusted to 40 ml with more AFG104 growth media. The samples were centrifuged for 10 minutes at 1350±50 RPM on low brake using an Allegra 6R centrifuge and swinging buckets. The supernatant was discarded and each pellet was re-suspended in a final volume of 30 ml AFG104 growth media. The total cell number and viability was determined for each sample. Cells were seeded at 60,000 cells/$cm^2$ in 1225 flasks in AFG104 growth media.

Cells were cultured in a humidified incubator set to 4% $O_2$, 5% $CO_2$ and 37° C. Cultures were fed with fresh AFG104 growth media on day 5 and harvested on day 8 (normal sheep bone marrow-derived cells) or day 9 (affected sheep bone marrow-derived cells). This first harvest was defined as passage 1 (P1) or Master Cell Bank (MCB). A portion of the cells were cryopreserved. The remaining cells were seeded at 60 cells/cm$^2$ and cultured for 5 days in AFG104 growth media a humidified incubator set to 4% $O_2$, 5% $CO_2$ and 37° C. They were fed on Day 5 with AFG104 growth media and harvested on day 9 (normal sheep bone marrow-derived cells) or day 8 (affected sheep bone marrow-derived cells). This next harvest was defined as passage 2 (P2) or Working Cell Bank 1 (WCB1). A portion of the cells were cryopreserved. The remaining cells were seeded at 60 cells/cm$^2$ and cultured for 5 days in AFG104 growth media a humidified incubator set to 4% $O_2$, 5%, $CO_2$ and 37° C. They were fed on Day 5 with AFG104 growth media and harvested on day 10 (normal and affected sheep bone marrow-derived cells). This next harvest was defined as passage 3 (P2) or Working Cell Bank 2 (WCB2). The doubling time for Normal Sheep bone marrow-derived cells was 22.14, 23.03 and 26.71 hours for MCB, WCB1, and WCB2 respectively. The doubling time for Affected Sheep bone-marrow derived cells was 22.19, 22.77 and 26.31 hours for MCB, WCB1, and WCB2 respectively. The culture doublings per passage were 8.67, 9.38, and 8.09 for Normal Sheep bone-marrow derived cells at MCB, WCB1 and WCB2 respectively. The culture doublings per passage were 89.73, 8.43, and 8.21 for Affected Sheep bone-marrow derived cells at MCB, WCB1 and WCB2 respectively.

It is to be appreciated that the Detailed Description section, and not the Summary and Abstract sections, is to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

Example 13

The following comparison data between Bovine and Ovine GM1 was generated by testing commercially available GM1 research materials (Avanti & Matreya) and GM1 material manufactured by Fidia. Fidia manufactured the same material that was used in previous clinical trials. All testing was performed in an R&D environment (non-GMP Equipment/non-validated Test Methods). The analytical work to date was performed during development of an Ovine derived GM1 drug product.

An HPLC method was developed to determine the relative amounts of the individual variants of GM1 molecules. Results indicate that GM1 molecules differ in the length of the alkyl chains that comprise the non-polar tail-group of each GM1 molecule. GM1 variant profile results are presented in Table 5 below. It was also observed that in all lots tested two variants are the dominant and make up over 80% of the total GM1 variants present. These are the d18:1 C18:0 and the d20:1 C18:0 variants.

TABLE 5

Distribution of Individual GM1 Species

| Supplier | Lot | Source | Peak Number | | | | | | | | | |
|---|---|---|---|---|---|---|---|---|---|---|---|---|
| | | | 1 | 2 | 3 | 4 | 5 | 6 | 7 | 8 | 9 | 10 |
| | | | | | | | Tentative ID | | | | | |
| | | | TBD | TBD | TBD | TBD | TBD | TBD | TBD | TBD | TBD | d18:1 C18:0 |
| Avanti | GM1-16 | Ovine | ND | ND | 0.28 | ND | 1.08 | 2.73 | ND | 0.72 | ND | 58.20 |
| Fidia | Unknown | Bovine | 0.29 | ND | 0.18 | ND | 0.71 | 0.29 | ND | 0.75 | ND | 33.62 |
| Matreya | 23012 | Bovine | ND | 0.81 | ND | 0.70 | 0.85 | 1.91 | 0.57 | 0.53 | 0.3 | 48.58 |

| Supplier | Lot | Source | Peak Number | | | | | | | | | |
|---|---|---|---|---|---|---|---|---|---|---|---|---|
| | | | 11 | 12 | 13 | 14 | 15 | 16 | 17 | 18 | 19 | 20 |
| | | | | | | | Tentative ID | | | | | |
| | | | TBD | TBD | d20:1 C18:0 | TBD | TBD | TBD | TBD | TBD | TBD | TBD |
| Avanti | GM1-16 | Ovine | 2.90 | 1.22 | 29.32 | 1.82 | 0.11 | 1.20 | 0.43 | ND | ND | ND |
| Fidia | Unknown | Bovine | 2.45 | 2.26 | 52.65 | 3.20 | 0.54 | 1.43 | 0.52 | 0.49 | 0.5 | 0.11 |
| Matreya | 23012 | Bovine | 3.10 | 1.57 | 36.11 | 1.87 | 0.59 | 1.46 | 0.26 | 0.45 | 0.31 | ND |

Assay values = Area % by HPLC
TBD = To be determined
ND = Not Detected

What is claimed is:

1. A method of producing GM1 ganglioside, comprising:
   (a) treating human bone marrow cells with chloroquine to accumulate GM1, wherein before said treatment with chloroquine, said bone marrow cells were cultured under low oxygen and low density conditions; and
   (b) isolating GM1 from said chloroquine-treated human bone marrow cells,
   wherein said treating human bone marrow cells results in an approximately 8-fold increase in GM1 production compared to human bone marrow cells not treated with chloroquine.

2. The method of claim 1, wherein said (a) treating said human bone marrow cells with chloroquine comprises contacting said human bone marrow cells with between 5 and 100 micromolar chloroquine.

3. The method of claim 1, wherein said (a) treating said human bone marrow cells with chloroquine comprises contacting said human bone marrow cells with chloroquine for between 2 to 72 hours.

4. The method of claim 1, wherein said human bone marrow cells are afflicted with GM1 gangliosidosis.

5. The method of claim 2, wherein said (a) treating said human bone marrow cells with chloroquine comprises contacting said human bone marrow cells with between 25 and 75 micromolar chloroquine.

6. The method of claim 2, wherein said (a) treating said human bone marrow cells with chloroquine comprises contacting said human bone marrow cells with between 40 and 50 micromolar chloroquine.

7. The method of claim 1, wherein said human bone marrow cells treated with chloroquine accumulate 65% more ganglioside than human bone marrow cells not treated with chloroquine.

* * * * *